(12) United States Patent
Staker et al.

(10) Patent No.: US 11,060,140 B2
(45) Date of Patent: Jul. 13, 2021

(54) SEQUENCING AND HIGH RESOLUTION IMAGING

(71) Applicant: Apton Biosystems, Inc., Pleasanton, CA (US)

(72) Inventors: Bryan P. Staker, San Ramon, CA (US); Niandong Liu, San Ramon, CA (US); Manohar R. Furtado, San Ramon, CA (US); Rixun Fang, Menlo Park, CA (US); Norman Burns, Pleasanton, CA (US); Windsor Owens, San Francisco, CA (US)

(73) Assignee: APTON BIOSYSTEMS, INC., Pleasanton, CA (US)

( * ) Notice: Subject to any disclaimer, the term of this patent is extended or adjusted under 35 U.S.C. 154(b) by 124 days.

(21) Appl. No.: 16/458,977

(22) Filed: Jul. 1, 2019

(65) Prior Publication Data

US 2019/0323080 A1    Oct. 24, 2019

Related U.S. Application Data

(63) Continuation of application No. 15/925,656, filed on Mar. 19, 2018, now Pat. No. 10,378,053.

(Continued)

(51) Int. Cl.
*C12Q 1/6874* (2018.01)
*G06T 7/73* (2017.01)
(Continued)

(52) U.S. Cl.
CPC ....... *C12Q 1/6874* (2013.01); *G06K 9/00127* (2013.01); *G06T 7/73* (2017.01); *G16B 25/30* (2019.02); *G16B 30/00* (2019.02); *G06K 9/0014* (2013.01); *G06K 9/00557* (2013.01); *G06T 2207/20056* (2013.01); *G06T 2207/30072* (2013.01)

(58) Field of Classification Search
None
See application file for complete search history.

(56) References Cited

U.S. PATENT DOCUMENTS 5,302,509 A    4/1994  Cheeseman
5,494,810 A    2/1996  Barany et al.
(Continued)

FOREIGN PATENT DOCUMENTS

BY    BY4655      9/2002
CN    1584592 A   2/2005
(Continued)

OTHER PUBLICATIONS

CAS Registry No. 361411-90-7 (entered into database 2001) (Year: 2001).
(Continued)

*Primary Examiner* — Justin P. Misleh
(74) *Attorney, Agent, or Firm* — Wilson Sonso Goodrich & Rosati

(57) ABSTRACT

Disclosed herein are methods and systems for detection and discrimination of optical signals from a densely packed substrate. These have broad applications for biomolecule detection near or below the diffraction limit of optical systems, including in improving the efficiency and accuracy of polynucleotide sequencing applications.

24 Claims, 21 Drawing Sheets

Related U.S. Application Data

(60) Provisional application No. 62/473,163, filed on Mar. 17, 2017.

(51) Int. Cl.
*G06K 9/00* (2006.01)
*G16B 25/30* (2019.01)
*G16B 30/00* (2019.01)

(56) References Cited

U.S. PATENT DOCUMENTS

| | | | |
|---|---|---|---|
| 5,763,594 | A | 6/1998 | Hiatt et al. |
| 6,103,474 | A | 8/2000 | Dellinger et al. |
| 6,214,987 | B1 | 4/2001 | Hiatt et al. |
| 6,232,465 | B1 | 5/2001 | Hiatt et al. |
| 6,654,505 | B2 | 11/2003 | Bridgham et al. |
| 6,852,487 | B1 | 2/2005 | Barany et al. |
| 7,057,026 | B2 | 6/2006 | Barnes et al. |
| 7,122,319 | B2 | 10/2006 | Liu et al. |
| 7,769,548 | B2 | 8/2010 | Garcia |
| 7,838,302 | B2 | 11/2010 | Zhuang et al. |
| 7,948,015 | B2 | 5/2011 | Rothberg et al. |
| 7,960,104 | B2 | 6/2011 | Drmanac et al. |
| 8,149,418 | B2 | 4/2012 | Tearney et al. |
| 8,158,346 | B2 | 4/2012 | Balasubramanian et al. |
| 8,175,452 | B1 | 5/2012 | Staker et al. |
| 8,428,454 | B2 | 4/2013 | Staker et al. |
| 8,676,013 | B2 | 3/2014 | Bouma et al. |
| 9,193,998 | B2 | 11/2015 | Khurana et al. |
| 1,037,805 | A1 | 8/2019 | Staker et al. |
| 1,051,043 | A1 | 12/2019 | Cai et al. |
| 1,082,981 | A1 | 11/2020 | Staker et al. |
| 10,829,816 | B2 * | 11/2020 | Staker ............ C12Q 1/6874 |
| 2002/0086322 | A1 | 7/2002 | Yu et al. |
| 2003/0118595 | A1 | 6/2003 | Niemeyer et al. |
| 2003/0207300 | A1 | 11/2003 | Matray et al. |
| 2003/0215862 | A1 | 11/2003 | Parce et al. |
| 2005/0049796 | A1 | 3/2005 | Webb et al. |
| 2005/0153320 | A1 | 7/2005 | Herron et al. |
| 2005/0250094 | A1 | 11/2005 | Storhoff et al. |
| 2007/0072208 | A1 | 3/2007 | Drmanac |
| 2008/0018898 | A1 | 1/2008 | Gunstream et al. |
| 2008/0161194 | A1 | 7/2008 | Turner et al. |
| 2009/0081688 | A1 | 3/2009 | Luo et al. |
| 2009/0317810 | A1 | 12/2009 | Lofton-Day et al. |
| 2010/0301398 | A1 | 12/2010 | Rothberg et al. |
| 2011/0009296 | A1 | 1/2011 | Kain et al. |
| 2011/0071048 | A1 | 3/2011 | Oshima |
| 2011/0165559 | A1 | 7/2011 | Lane et al. |
| 2012/0020537 | A1 | 1/2012 | Garcia et al. |
| 2012/0052490 | A1 | 3/2012 | Eid et al. |
| 2012/0307121 | A1 | 12/2012 | Lu et al. |
| 2012/0330567 | A1 | 12/2012 | Bauer et al. |
| 2013/0045872 | A1 | 2/2013 | Zhou et al. |
| 2013/0053256 | A1 | 2/2013 | Hubbell |
| 2013/0059740 | A1 | 3/2013 | Drmanac et al. |
| 2013/0124100 | A1 | 5/2013 | Drmanac et al. |
| 2013/0265459 | A1 | 10/2013 | Duparre et al. |
| 2014/0194311 | A1 | 7/2014 | Gullberg et al. |
| 2014/0287468 | A1 | 9/2014 | Richard |
| 2015/0152473 | A1 | 6/2015 | Nadeau et al. |
| 2015/0267251 | A1 | 9/2015 | Cai et al. |
| 2015/0330974 | A1 | 11/2015 | Staker et al. |
| 2016/0003809 | A1 | 1/2016 | Dunaway |
| 2016/0201119 | A1 | 7/2016 | Staker et al. |
| 2017/0152554 | A1 | 6/2017 | Drmanac et al. |
| 2018/0023124 | A1 * | 1/2018 | Collins ............ C12Q 1/6827 435/6.11 |
| 2019/0276886 | A1 | 9/2019 | Skinner et al. |
| 2019/0284552 | A1 * | 9/2019 | Collins ............ C12Q 1/6837 |
| 2020/0140933 | A1 | 5/2020 | Staker et al. |
| 2020/0217850 | A1 | 7/2020 | Liu et al. |
| 2020/0393691 | A1 | 12/2020 | Owens et al. |

FOREIGN PATENT DOCUMENTS

| | | |
|---|---|---|
| CN | 1653480 A | 8/2005 |
| CN | 101865843 A | 10/2010 |
| CN | 101865843 B | 5/2012 |
| EP | 1388587 A4 | 12/2006 |
| EP | 2251435 A1 | 11/2010 |
| JP | 2002524739 A | 8/2002 |
| JP | 2007536528 A | 12/2007 |
| JP | 2008249711 A | 10/2008 |
| WO | WO-9967641 A2 | 12/1999 |
| WO | WO-9967641 A3 | 3/2000 |
| WO | WO-2005113817 A9 | 8/2006 |
| WO | WO-2007097754 A1 | 8/2007 |
| WO | WO-2008033167 A2 | 3/2008 |
| WO | WO-2011137183 A1 | 11/2011 |
| WO | WO-2012031011 A1 | 3/2012 |
| WO | WO-2014015269 A1 | 1/2014 |
| WO | WO-2014078855 A1 | 5/2014 |
| WO | WO-2015027112 A1 | 2/2015 |
| WO | WO-2016074338 A1 | 5/2016 |
| WO | WO-2016134191 A1 | 8/2016 |
| WO | WO-2016156845 A1 | 10/2016 |
| WO | WO-2017079573 A1 | 5/2017 |
| WO | WO-2017079593 A1 | 5/2017 |
| WO | WO-2017123770 A1 | 7/2017 |
| WO | WO-2017161251 A1 | 9/2017 |
| WO | WO-2017196527 A1 | 11/2017 |
| WO | WO-2017223041 A1 | 12/2017 |
| WO | WO-2018161013 A1 | 9/2018 |
| WO | WO-2018170518 A1 | 9/2018 |
| WO | WO-2018175402 A1 | 9/2018 |

OTHER PUBLICATIONS

Cho et al. Optimization of Aptamer Microarray Technology for Multiple Protein Targets. Analytica Chimica Acta 564(1):82-90 (2006).

Drmanac et al. Human Genome Sequencing Using Unchained Base Reads on Self-Assembling DNA nanoarrays. Science Reports, 327:78-81 (Jan. 1, 2010).

Gavrilovic et al. Quantification of Colocalization and Cross-Tk Based on Spectral Angles. J Microsc 324(3):311-324 (2009).

Gunderson et al., Decoding randomly ordered DNA arrays. Genome Research. 14(5):870-877 (2004).

Guo et al. Four-color DNA sequencing with 3'-O-modified nucleotide reversible terminators and chemically cleavable fluorescent dideoxynucleotides. PNAS USA 105(27):9145-9150 (2008).

Guo et al. Supporting Information for Four-color DNA sequencing with 3'-O-modified nucleotide reversible terminators and chemically cleavable fluorescent dideoxynucleotides. PNAS USA PNAS USA 105(27):9145-9150 (2008).

Hager et al. Arrays of Individual DNA Molecules on Nanopatterned Substrates. Scientific Reports 7:42075 (2017).

Illumina Sequencing Technology, Technology Spotlight: Illumina® Sequencing, Illumina, Inc. (2010).

Ju et al. Four-Color DNA Sequencing by Synthesis Using Cleavable Fluorescent Nucleotide Reversible Terminators. PNAS USA 103:19635-19640 (2006).

Kao et al. BayesCall: A Model-Based Base-Cling algorithm for High-Throughput Short-Read Sequencing. Genome Research 19:1884-1895 (2009).

Kumar et al. PEG-Labeled Nucleotides and Nanopore Detection for Single Molecule DNA Sequencing by Synthesis. Scientific Reports 2:1-8 (2012).

Lee et al., Ion-sensitive field-effect transistor for biological sensing. Sensors. 9(9):7111-7131 (2009).

Levene et al., Zero-mode waveguides for single-molecule analysis at high concentrations. Science. 299(5607)682-686 (2003).

Levy et al. Advancements in Next-Generation Sequencing. Annu Rev Genomics Hum Genet 17:95-115 (2016).

Liu et al. Comparison of Next-Generation Sequencing Systems. J Biomed Biotechnol 2012: 251364 (2012).

(56) References Cited

OTHER PUBLICATIONS

Moerner, et al., Methods of single-molecule fluorescence spectroscopy and microscopy. Review of Scientific Instruments. 74(8):3597-3619 (2003).
PCT/US2013/070797 International Preliminary Report on Patentability dated Jan. 16, 2015.
PCT/US2013/070797 International Search Report and Written Opinion dated Feb. 21, 2014.
PCT/US2014/052186 International Preliminary Report on Patentability dated Sep. 21, 2015.
PCT/US2014/052186 International Search Report and Written Opinion dated Dec. 17, 2014.
PCT/US2018/023187 International Search Report and Written Opinion dated May 31, 2018.
PCT/US2018/023310 International Preliminary Report on Patentability dated Sep. 24, 2019.
PCT/US2018/023310 International Search Report and Written Opinion dated Sep. 4, 2018.
Riley et al. Reed-Solomon Codes. https://www.cs.cmu.edu/-guyb/realworld/reedsolomon/reedsolomoncodes.html (1996).
Rotman, B., Measurement of activity of single molecules of beta-D-galactosidase. Proceedings of the National Academy of Sciences of the United States of America. 47:1981-1991 (1961).
Song et al., Aptamer-based biosensors. Trends in Analytical Chemistry. 27(2)108-117 (2008).
U.S. Appl. No. 14/443,655 Office Action dated Jun. 12, 2018.
U.S. Appl. No. 14/443,655 Office Action dated Jun. 25, 2019.
U.S. Appl. No. 14/443,655 Office Action dated Mar. 9, 2017.
U.S. Appl. No. 14/443,655 Office Action dated Nov. 14, 2016.
U.S. Appl. No. 14/443,655 Office Action dated Oct. 18, 2017.
U.S. Appl. No. 14/912,883 Office Action dated Apr. 3, 2019.
U.S. Appl. No. 15/925,656 Office Action dated Sep. 27, 2018.
Gu, et al. Multiplex single-molecule interaction profiling of DNA-barcoded proteins. Nature. Nov. 27, 2014;515(7528):554-7. doi: 10.1038/nature13761. Epub Sep. 21, 2014.
Kozlov, et al. Efficient strategies for the conjugation of oligonucleotides to antibodies enabling highly sensitive protein detection. Biopolymers. Apr. 5, 2004;73(5):621-30.
PCT/US2019/015243 International Search Report and Written Opinion dated Mar. 22, 2019.
PCT/US2019/051796 International Search Report and Written Opinion dated Jan. 3, 2020.
Svobodova et al., Comparison of Different Methods for Generation of Single-Stranded DNA for SELEX Processes. Anal Bioanal Chem 404(3): 835-842 (2012).
Tuerk. Systematic evolution of ligands by exponential enrichment: RNA ligands to bacteriophage T4 DNA polymerase. Science 249:505-510 (1990).
U.S. Appl. No. 16/572,535 Non-Final Office Action dated Mar. 30, 2020.
U.S. Appl. No. 14/912,883 Final Office Action dated Jan. 3, 2020.
U.S. Appl. No. 17/084,017 Office Action dated Feb. 2, 2021.

* cited by examiner

| Parameter | Unit | Case 1 | Case 2 | Case 3 | Case 4 | Case 5 | Case 6 |
|---|---|---|---|---|---|---|---|
| *Inputs* | | | | | | | |
| Pitch | nm | 220 | 236 | 261 | 200 | 250 | 333 |
| # Molecules / um^2 | NA | 20.7 | 17.9 | 14.7 | 25.0 | 16.0 | 9.0 |
| # Cycles | NA | 100 | 100 | 100 | 100 | 100 | 100 |
| Lane width | mm | 63 | 63 | 63 | 63 | 63 | 63 |
| Lane length | mm | 63 | 63 | 63 | 63 | 63 | 63 |
| Frame rate | Hz | 85 | 85 | 85 | 85 | 85 | 85 |
| *Outputs* | | | | | | | |
| Throughput (30X genome) | per run | 90 | 78 | 64 | 109 | 70 | 39 |
| Throughput (30X genome) | per day | 93 | 81 | 66 | 113 | 72 | 41 |
| Throughput (Gb) | per run | 8,127 | 7,044 | 5,785 | 9,838 | 6,297 | 3,542 |
| Throughput (Gb) | per day | 8,398 | 7,280 | 5,978 | 10,167 | 6,507 | 3,660 |
| # Spots / chip | 10^9 | 81.3 | 70.4 | 57.9 | 98.4 | 63.0 | 35.4 |
| Imaging time per cycle | min | 13.9 | 13.9 | 13.9 | 13.9 | 13.9 | 13.9 |

Figure 1

SEQUENCING AND HIGH RESOLUTION IMAGING

CROSS-REFERENCE TO RELATED APPLICATIONS

This application is a continuation of U.S. application Ser. No. 15/925,656, filed Mar. 19, 2018, which claims the benefit of U.S. Provisional Application No. 62/473,163, filed Mar. 17, 2017, the entire disclosures of which are hereby incorporated by reference in their entirety for all purposes.

BACKGROUND

Reducing the cost of sequencing is important to enable improved healthcare. A standard for measuring the cost of sequencing is the price of a 30× human genome, defined as 90 gigabases.

The price of a genome dropped significantly from 2007 to 2011 where it stabilized to just under $10,000 per genome. A significant milestone has been the $1,000 genome which was recently achieved. The next major milestone is the $100 genome which is expected to take several years. This invention discusses methods to achieve a $10 genome in a substantially contracted time frame. At this price point, it will be economical to sequence every newborn and will make the cost barrier for disease diagnosis and screening, especially in the area of oncology, significantly more economical.

The major cost components for sequencing systems are primarily the consumables which include biochip and reagents and secondarily the instrument costs.

To reach a $10 30× genome, a 100 fold cost reduction, the amount of data per unit area needs to increase by 100 fold and the amount of reagent per data point needs to drop by 100 fold.

In an example $1,000 genome platform with cluster densities of ten million molecules per square centimeter, each molecule occupies on average 10 um$^2$ of chip area. Thus, the average effective pitch is 3,160 nm. If densities 100 fold higher could be obtained with 100 fold fewer copies, for the same chip area and reagent a 100 fold more information would be obtained resulting in 100 fold reduction in costs. At 100 fold higher density, the new pitch would need to be 320 nm. The number of copies to equalize reagent use is 10 copies per molecule, 100 fold fewer than 1,000 copies per cluster.

Thus, what is needed are optical imaging systems that can resolve optical signals from single molecules spaced apart by around 320 nm. However, this resolution is challenging to achieve due to the diffraction limit of light, which is defined by $\lambda/(2*N.A.)$, where $\lambda$ is the wavelength of light, and N.A. is the numerical aperture of the optical imaging system, which is near 1 in aqueous-based systems, such as those useful for sequencing and analyte detection. Thus, for detection of optical signals emitted around 650 nm, the 320 nm spacing is near or below the diffraction limit, which can prevent resolving individual features on such an array.

Although other methods exist that are not constrained by the diffraction limit of optical signals, such as electrical based systems developed by companies such as Ion Torrent (purchased by Thermo Fisher) and Oxford Nanopore, image based sequencing systems currently have the lowest sequencing costs of all existing sequencing technologies. Image based systems achieve low cost through the combination of high throughput imaging optics and low cost consumables.

What is needed, therefore, are optical imaging methods and systems that overcome the diffraction limit to facilitate increased resolution of individual features on a closely-packed substrate, such that resolution below the diffraction limit can be done with high accuracy. These methods and systems can have particular applications in high resolution feature detection, including for use in optical imaging for polynucleotide sequence detection.

SUMMARY OF THE INVENTION

Methods and systems for sub-diffraction limited imaging of single molecule analytes immobilized to the surface of a substrate. Substrates include flow cells and the like for performing binding reactions with the analytes. Analytes include biomolecules spaced apart on the surface at discrete locations for single molecule resolution, such as individual polynucleotides or proteins. These can be used for high resolution single molecule detection for such applications as single molecule sequencing by synthesis.

In some embodiments, provided herein is a method for sequencing a plurality of polynucleotides immobilized at high density on a surface of a substrate at a single molecule resolution, comprising: providing a substrate comprising a surface, wherein the surface comprises a plurality of polynucleotides immobilized on the surface at discrete locations, and wherein said surface comprises reagents for sequencing by synthesis; performing a plurality of cycles of single molecule sequencing by synthesis comprising, each cycle comprising: contacting said polynucleotides with a set of reversible terminator nucleotides comprising a detectable label; imaging a field of said surface with an optical system to detect an optical signal from each nucleotide incorporated into said polynucleotides, thereby detecting a plurality of optical signals in said field for said cycle; determining a peak location from each of said plurality of optical signals from images of said field from at least two of said plurality of cycles; overlaying said peak locations for each optical signal and applying an optical distribution model at each cluster of optical signals to determine a relative position of each detected analyte on said surface with improved accuracy; deconvolving said optical signals in each field image from each cycle using said determined relative position and a deconvolution function; identifying said detectable labels incorporated into said polynucleotide for each field and each cycle from said deconvolved optical signals; and sequencing said plurality of polynucleotides immobilized on the surface of the substrate from said identified detectable labels across said plurality of cycles at each polynucleotide position.

In some embodiments, the substrate comprises 1,000 or less, 500 or less, 100 or less, 50 or less 25 or less, 20 or less, 15 or less, or 10 or less clonal copies of a single molecule comprising an identical sequence. In some embodiments, the polynucleotides are DNA concatemers.

In some embodiments, each cycle further comprises washing said surface to remove unbound nucleotides after contacting said surface with said plurality of reversible terminator nucleotides and before imaging said field. In some embodiments, the cycle further comprises cleaving said reversible terminator if another cycle is to be performed. In some embodiments, the cycle further comprises cleaving said detectable label if another cycle is to be performed.

In some embodiments, the set of reversible terminator nucleotides comprises at least two distinct nucleotides each with a distinct detectable label. In some embodiments, the set of reversible terminator nucleotides comprise at least four distinct nucleotides each with a distinct detectable label. In some embodiments, the set of reversible terminator nucleotides comprises adenine, cytosine, thymine, and guanine. In some embodiments, the set of reversible terminator nucleotides comprises adenine, cytosine, uracil, and guanine.

In some embodiments, the polynucleotide comprises deoxyribonucleic acid or ribonucleic acid. In some embodiments, the plurality of target polynucleotides have a length of about 1 kb to about 100 kb. In some embodiments, the plurality of target polynucleotides have a length of about 10 kb to about 50 kb. In some embodiments, the polynucleotides bound to the surface are separated by a distance of at least 10 nm.

In some embodiments, the detectable label is bound to the 3'-OH group of said reversible terminator nucleotide. In some embodiments, a blocking group that is not a detectable label is bound to the 3'-OH of said reversible terminator nucleotide.

In some embodiments, the plurality of target polynucleotides are immobilized by binding to capture probes bound to said surface at discrete locations. In some embodiments, the plurality of target polynucleotides are linked to an adaptor comprising a capture sequence that is complementary to a sequence of said capture probe, and a priming sequence that is complementary to a sequence of said sequencing primer. In some embodiments, the capture sequence is from 20 to 50 mer. In some embodiments, the priming sequence is from 20 to 50 mer.

In some embodiments, the method of sequencing further comprises performing previous cycle regression to correct a phasing error by comparing a set of polynucleotides having the same sequence or on the basis of the data itself.

In some embodiments, the deconvolution comprises removing interfering optical signals from neighboring polynucleotides using a center-to-center distance between said neighboring polynucleotides from said determined relative positions. In some embodiments, the deconvolution function comprises nearest neighbor variable regression. In some embodiments, the deconvolution comprises separating overlapping wavelengths from each unique detectable label used in each cycle. In some embodiments, the deconvolution function comprises cross-talk regression. In some embodiments, the deconvolution function comprises nearest neighbor variable regression, smoothing, or cross-talk correction.

Polynucleotides

In some embodiments, the polynucleotides are spaced apart on said substrate for single molecule sequencing by synthesis. In some embodiments, the polynucleotides are densely packed on said substrate such that there is overlap between optical signals emitted by said detectable labels from probes bound to adjacent polynucleotides comprising distinct polynucleotide sequences to be sequenced. In some embodiments, the polynucleotides immobilized on said surface are spaced apart on average of less than the diffraction limit of the light emitted by the detectable labels and imaged by the optical system. In some embodiments, at least two of said polynucleotides immobilized on said surface are spaced apart less than the diffraction limit of the light emitted by the detectable labels and imaged by the optical system. In some embodiments, at least 10%, 20%, 30%, 40%, 50%, 60%, 70%, 80%, or 90% of said polynucleotides immobilized on said surface are spaced apart from another immobilized polynucleotide by less than the diffraction limit of the light emitted by the detectable labels and imaged by the optical system.

In some embodiments, the optical system comprises a numerical aperture of between 0.2-2.0. In some embodiments, the optical system comprises a numerical aperture of between 1-1.1. In some embodiments, the wavelength of said emitted light is about 400-450 nm, about 450-500 nm, about 500-550 nm, about 550-600 nm, about 600-650 nm, or about 650-700 nm.

In some embodiments, the immobilized polynucleotides comprises a minimum center-to-center distance between adjacent polynucleotides of less than 600 nm, less than 500 nm, less than 400 nm, less than 300 nm, or less than 200 nm. In some embodiments, the polynucleotides are immobilized on said surface at an average density of about 4-25 molecules per square micron. In some embodiments, the polynucleotides are immobilized on said surface at an average density of more than 4, more than 6, more than 8, more than 10, more than 15, or more than 20 molecules per square micron.

In some embodiments, the imaging of said surface is performed at a resolution greater than the critical sampling rate as determined by the Nyquist limit of the optical system. In some embodiments, the imaging of said surface is performed at a resolution of at least 2× the Nyquist sampling frequency. In some embodiments, the imaging of said surface is performed at a resolution of one pixel per 300 nm or higher along an axis of the image field. In some embodiments, the imaging of said surface is performed at a resolution of about 162.5 nm per pixel along an axis of the image field.

In some embodiments, the sequencing method further comprises generating an oversampled image with a higher pixel density from each of said field images from each cycle. In some embodiments, the oversampled image is generated by applying smoothing to each field image based on an anticipated point spread function for said optical signals. In some embodiments, a data set comprising the location of optical signal peaks from said image is generated from said field image or said oversampled image.

In some embodiments, overlaying said peak locations comprises aligning positions of said optical signal peaks detected in each field for a plurality of said cycles to generate a cluster of optical peak positions for each polynucleotide from said plurality of cycles. In some embodiments, the optical distribution model is a Gaussian distribution. In some embodiments, the optical distribution model is a point spread function.

In some embodiments, the relative position is determined for a plurality of said polynucleotides in said field. In some embodiments, the relative position is determined with an accuracy of within 10 nm RMS.

In some embodiments, the sequencing method further comprises overlaying a plurality of images of said field from different cycles to determine a relative offset with respect to a reference image of said field. In some embodiments, the method comprises generating offset values for each of said fields aligned with said reference field. In some embodiments, the relative position of polynucleotides within each field is determined from said offset values. In some embodiments, the offset determination comprises discarding field images whose alignment is outside of an alignment threshold. In some embodiments, the sequencing method comprises overlaying a plurality of images from said field to determine a relative offset with respect to a reference image of said field, wherein said relative position is determined with an accuracy of within 5 nm RMS.

In some embodiments, the method is capable of resolving optical signals from a surface at a density of ~4-25 per square micron.

In some embodiments, the detectable labels emit light, and the polynucleotides are immobilized on the surface of said substrate at an average pitch below the diffraction limit of light emitted from said detectable labels.

According to some embodiments, also provided herein is a method for accurately determining a relative position of analytes immobilized on the surface of a densely packed substrate, comprising: providing a substrate comprising a surface, wherein the surface comprises a plurality of analytes immobilized on the surface at discrete locations; performing a plurality of cycles of probe binding and signal detection on said surface, (each cycle comprising: contacting said analytes with a plurality of probes from a probe set, wherein said probes comprise a detectable label, wherein each of said probes binds specifically to a target analyte; and imaging a field of said surface with an optical system to detect a plurality of optical signals from individual probes bound to said analytes at discrete locations on said surface); determining a peak location from each of said plurality of optical signals from images of said field from at least two of said plurality of cycles; and overlaying said peak locations for each optical signal and applying an optical distribution model at each cluster of optical signals to determine a relative position of each detected analyte on said surface with improved accuracy.

In some embodiments, the method further comprises: deconvolving said optical signals in each field image from each cycle using said determined relative position and a deconvolution function; and identifying said detectable labels bound to said immobilized analytes for each field and each cycle from said deconvolved optical signals.

In some embodiments, the method further comprises using said detectable label identity for each analyte detected at each cycle to identify a plurality of said analytes on said substrate.

In some embodiments, the deconvolution comprises removing interfering optical signals from neighboring analytes using a center-to-center distance between said neighboring analytes from said determined relative positions of said neighboring analytes.

In some embodiments, the deconvolution function comprises nearest neighbor variable regression. In some embodiments, the deconvolution comprises separating overlapping wavelengths from each unique detectable label used in each cycle. In some embodiments, the deconvolution function comprises cross-talk regression. In some embodiments, the deconvolution function comprises nearest neighbor variable regression, smoothing, or cross-talk correction.

In some embodiments, the analytes are single molecules. In some embodiments, the single molecules are single biomolecules. In some embodiments, the single molecules are polynucleotides.

In some embodiments, the analytes are densely packed on said substrate such that there is overlap between optical signals emitted by said detectable labels from probes bound to adjacent analytes. In some embodiments, the analytes immobilized on said surface are spaced apart on average less than the diffraction limit of the light emitted by the detectable labels and imaged by the optical system. In some embodiments, at least two of said analytes immobilized on said surface are spaced apart less than the diffraction limit of the light emitted by the detectable labels and imaged by the optical system. In some embodiments, at least 10%, 20%, 30%, 40%, 50%, 60%, 70%, 80%, or 90% of said analytes immobilized on said surface are spaced apart from another analyte by less than the diffraction limit of the light emitted by the detectable labels and imaged by the optical system.

In some embodiments, the optical system comprises a numerical aperture of between 0.2-2.0. In some embodiments, the optical system comprises a numerical aperture of between 1-1.1. In some embodiments, the wavelength of said light is about 400-450 nm, about 450-500 nm, about 500-550 nm, about 550-600 nm, about 600-650 nm, or about 650-700 nm.

In some embodiments, the immobilized analytes comprises a minimum center-to-center distance between adjacent analytes of less than 600 nm, less than 500 nm, less than 400 nm, less than 300 nm, or less than 200 nm. In some embodiments, the target analytes are immobilized on said surface at an average density of about 4-25 molecules per square micron. In some embodiments, the target analytes are immobilized on said surface at an average density of more than 4, more than 6, more than 8, more than 10, more than 15, or more than 20 molecules per square micron.

In some embodiments, each cycle further comprises repeating steps i) and ii) using additional probes from said probe set. In some embodiments, each cycle further comprises removing unbound probes from said surface after contacting said surface with said plurality of probes and before imaging said field. In some embodiments, each cycle further comprises removal of bound probes from said surface if another cycle is to be performed.

In some embodiments, at least 5, 10, 15, 20, 25, 30, 35, 40, 50, 60, 70, 80, 90, or 100 cycles are performed. In some embodiments, each cycle comprises imaging a plurality of fields of said surface with said optical system.

In some embodiments, the imaging of said surface is performed at a resolution greater than the critical sampling rate as determined by the Nyquist limit of the optical system. In some embodiments, the imaging of said surface is performed at a resolution of at least 2× the Nyquist sampling frequency. In some embodiments, the imaging of said surface is performed at a resolution of one pixel per 300 nm or higher along an axis of the image field. In some embodiments, the imaging of said surface is performed at a resolution of about 162.5 nm per pixel along an axis of the image field.

In some embodiments, the method further comprises generating an oversampled image with a higher pixel density from each of said field images from each cycle. In some embodiments, the oversampled image is generated by applying smoothing to each field image based on an anticipated point spread function for said optical signals. In some embodiments, the method further comprises generating a data set comprising the location of optical signal peaks from said field image or said oversampled image.

In some embodiments, overlaying said peak locations comprises aligning positions of said optical signal peaks detected in each field for a plurality of said cycles to generate a cluster of optical peak positions for each analyte from said plurality of cycles. In some embodiments, the optical distribution model is a Gaussian distribution. In some embodiments, the optical distribution model is a point spread function.

In some embodiments, the relative position is determined for a plurality of said analytes in said field. In some embodiments, the relative position is determined with an accuracy of within 10 nm RMS.

In some embodiments, the method further comprises overlaying a plurality of images of said field from different cycles to determine a relative offset with respect to a reference image of said field. In some embodiments, the method comprises generating offset values for each of said fields aligned with said reference field. In some embodiments, the relative position of analytes within each field is determined from said offset values. In some embodiments, the method further comprises discarding field images whose alignment is outside of an alignment threshold. In some embodiments, the method further comprises overlaying a plurality of images from said field to determine a relative offset with respect to a reference image of said field, wherein said relative position is determined with an accuracy of within 5 nm RMS.

In some embodiments, the method is capable of resolving optical signals from a surface at a density of ~4-25 per square micron.

In some embodiments, the detectable labels emit light, and wherein the target analytes bound to said array comprises an average pitch below the diffraction limit of light emitted from said detectable labels.

Also provided herein, according to some embodiments, is a method for identifying a plurality of densely packed analytes immobilized on a surface of a substrate, comprising: providing a substrate comprising a surface, wherein the surface comprises a plurality of analytes immobilized on the surface at discrete locations; performing a plurality of cycles of probe binding and signal detection on said surface, (each cycle comprising: contacting said analytes with a plurality of probes from a probe set, wherein said probes comprise a detectable label, wherein each of said probes binds specifically to a target analyte; and imaging a field of said surface with an optical system to detect a plurality of optical signals from individual probes bound to said analytes); determining a peak location from each of said plurality of optical signals from images of said field from at least two of said plurality of cycles; overlaying said peak locations for each optical signal and applying an optical distribution model at each cluster of optical signals to determine a relative position of each detected analyte on said surface with improved accuracy; deconvolving said optical signals in each field image from each cycle using said determined relative position and a deconvolution function; determining the identity of each detectable label in each field and each cycle from said deconvolved optical signals; and using said detectable label identity for each analyte detected at each cycle to identify a plurality of said analytes on said substrate.

Also provided herein, according to some embodiments, is a system for determining the identity of a plurality of analytes, comprising an optical imaging device configured to image a plurality of optical signals from a field of a substrate over a plurality of cycles of probe binding to analytes immobilized on a surface of the substrate; and an image processing module, said module configured to: determine a peak location from each of said plurality of optical signals from images of said field from at least two of said plurality of cycles; determine a relative position of each detected analyte on said surface with improved accuracy by applying an optical distribution model to each cluster of optical signals from said plurality of cycles; and deconvolve said optical signals in each field image from each cycle using said determined relative position and a deconvolution function.

In some embodiments, the image processing module is further configured to determine an identity of said analytes immobilized on said surface using said deconvolved optical signals.

In some embodiments, the analytes are each a polynucleotide molecule and wherein said identity comprises a sequence of said polynucleotide molecules.

In some embodiments, the optical image device comprises a moveable stage defining a scannable area.

In some embodiments, the optical image device comprises a sensor and optical magnification configured to sample a surface of a substrate at below the diffraction limit in said scannable area.

In some embodiments, the optical imaging system further comprising a substrate comprising analytes immobilized to a surface of the substrate at a center-to-center spacing below the diffraction limit.

In some embodiments, the deconvolution comprises removing interfering optical signals from neighboring analytes using a center-to-center distance between said neighboring analytes from said determined relative positions of said neighboring analytes. In some embodiments, the deconvolution function comprises nearest neighbor variable regression. In some embodiments, the deconvolution comprises separating overlapping wavelengths from each unique detectable label used in each cycle. In some embodiments, the deconvolution function comprises cross-talk regression. In some embodiments, the deconvolution function comprises nearest neighbor variable regression, smoothing, or cross-talk correction.

In some embodiments, the analytes are single molecules. In some embodiments, the single molecules are single biomolecules. In some embodiments, the single molecules are polynucleotides.

In some embodiments, the analytes are densely packed on said substrate such that there is overlap between optical signals emitted by said detectable labels from probes bound to adjacent analytes. In some embodiments, the analytes immobilized on said surface are spaced apart on average less than the diffraction limit of the light emitted by the detectable labels and imaged by the optical system. In some embodiments, at least two of said analytes immobilized on said surface are spaced apart less than the diffraction limit of the light emitted by the detectable labels and imaged by the optical system. In some embodiments, at least 10%, 20%, 30%, 40%, 50%, 60%, 70%, 80%, or 90% of said analytes immobilized on said surface are spaced apart from another analyte by less than the diffraction limit of the light emitted by the detectable labels and imaged by the optical system.

In some embodiments, the optical system comprises a numerical aperture of between 0.2-2.0. In some embodiments, the optical system comprises a numerical aperture of between 1-1.1. In some embodiments, the wavelength of said light detected by the optical system is about 400-450 nm, about 450-500 nm, about 500-550 nm, about 550-600 nm, about 600-650 nm, or about 650-700 nm.

In some embodiments, the immobilized analytes comprises a minimum center-to-center distance between adjacent analytes of less than 600 nm, less than 500 nm, less than 400 nm, less than 300 nm, or less than 200 nm. In some embodiments, the analytes are immobilized on said surface at an average density of about 4-25 molecules per square micron. In some embodiments, the analytes are immobilized on said surface at an average density of more than 4, more than 6, more than 8, more than 10, more than 15, or more than 20 molecules per square micron.

In some embodiments, the optical imaging device is configured to image said substrate at a resolution greater than the critical sampling rate as determined by the Nyquist limit of the optical system. In some embodiments, the optical imaging device is configured to image said substrate at a resolution of at least 2× the Nyquist sampling frequency. In some embodiments, the optical imaging device is configured to image said substrate at a resolution of no more than 300 nm per pixel along an axis of the image field. In some embodiments, the optical imaging device is configured to image said substrate at a resolution of about 162.5 nm per pixel along an axis of the image field.

In some embodiments, the image processing module is configured to generate an oversampled image with a higher pixel density from each of said field images from each cycle. In some embodiments, the image processing module is configured to apply smoothing to each field image based on an anticipated point spread function for said optical signals to generate said oversampled image. In some embodiments, the image processing module is configured to generate a data set comprising the location of optical signal peaks from said imaged field.

In some embodiments, the system is capable of resolving optical signals from a surface at a density of ~4-25 per square micron.

In some embodiments, the target analytes are immobilized on said substrate at an average center-to-center distance below the diffraction limit of light detected by the optical imaging device.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 1 shows sequencer throughput versus array pitch and outlines a system design which meets the criteria needed for a $10 genome.

FIG. 13B shows a cross-talk plot for the same imaging region but with deconvolution and nearest neighbor regression performed as shown in FIG. 11 and described herein.

DETAILED DESCRIPTION

Figure 2A:
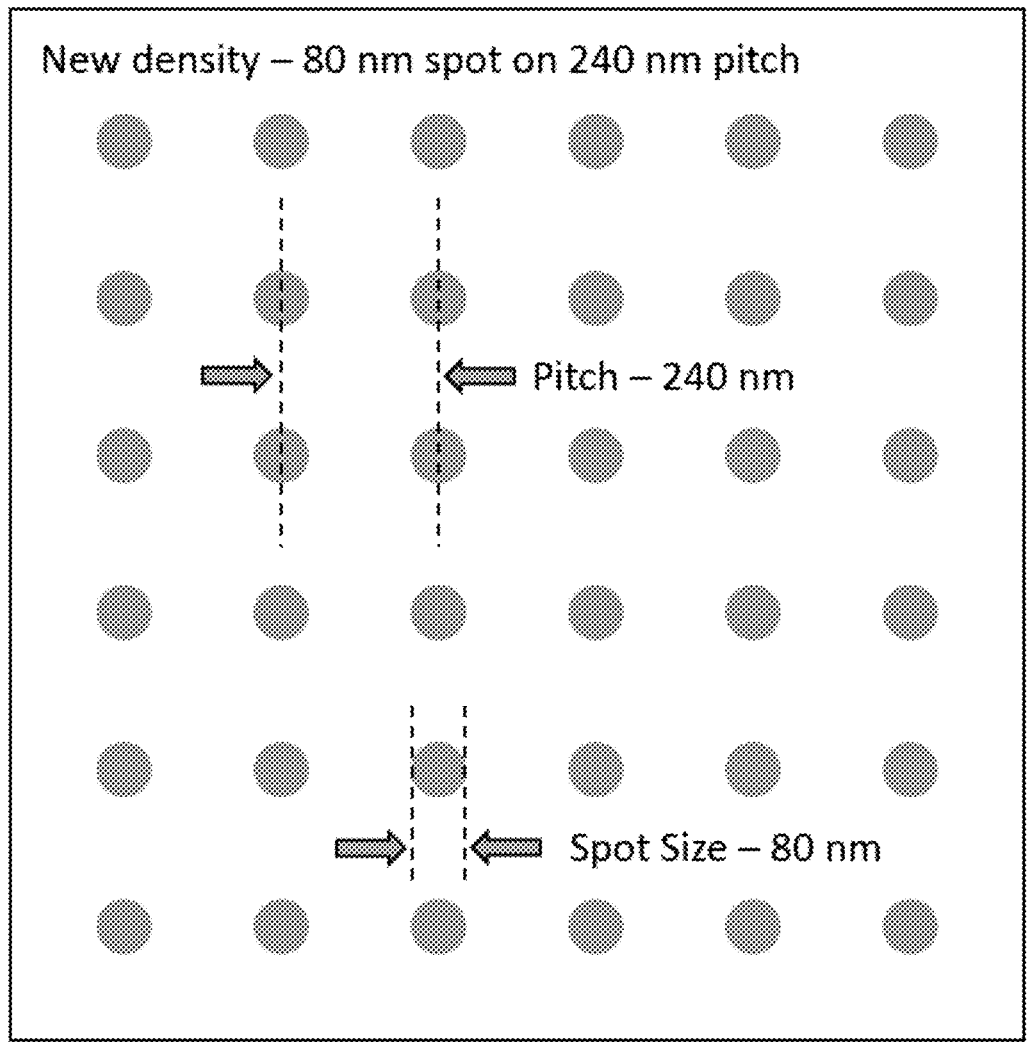
FIG. 2A shows a proposed embodiment of a high-density region of 80 nm diameter binding regions (spots) on a 240 nm pitch for low cost sequencing.

The details of various embodiments of the invention are set forth in the description below. Other features, objects, and advantages of the invention will be apparent from the description and the drawings, and from the claims.

Definitions

As used herein, the term center-to-center distance refers to a distance between two adjacent molecules as measured by the difference between the average position of each molecule on a substrate. The term average minimum center-to-center distance refers specifically to the average distance between the center of each analyte disposed on the substrate and the center of its nearest neighboring analyte, although the term center-to-center distance refers also to the minimum center-to-center distance in the context of limitations corresponding to the density of analytes on the substrate. As used herein, the term "pitch" or "average effective pitch" is generally used to refer to average minimum center-to-center distance. In the context of regular arrays of analytes, pitch may also be used to determine a center-to-center distance between adjacent molecules along a defined axis.

As used herein, the term "overlaying" (e.g., overlaying images) refers to overlaying images from different cycles to generate a distribution of detected optical signals (e.g., position and intensity, or position of peak) from each analyte over a plurality of cycles. This distribution of detected optical signals can be generated by overlaying images, overlaying artificial processed images, or overlaying datasets comprising positional information. Thus, as used herein, the term "overlaying images" encompasses any of these mechanisms to generate a distribution of position information for optical signals from a single probe bound to a single analyte for each of a plurality of cycles.

A "cycle" is defined by completion of one or more passes and stripping of the detectable label from the substrate. Subsequent cycles of one or more passes per cycle can be performed. For the methods and systems described herein, multiple cycles are performed on a single substrate or sample. For DNA sequencing, multiple cycles requires the use of a reversible terminator and a removable detectable label from an incorporated nucleotide. For proteins, multiple cycles requires that the probe removal (stripping) conditions either maintain proteins folded in their proper configuration, or that the probes used are chosen to bind to peptide sequences so that the binding efficiency is independent of the protein fold configuration.

A "pass" in a detection assay refers to a process where a plurality of probes comprising a detectable label are introduced to the bound analytes, selective binding occurs between the probes and distinct target analytes, and a plurality of signals are detected from the detectable labels. A pass includes introduction of a set of antibodies that bind specifically to a target analyte. A pass can also include introduction of a set of labelled nucleotides for incorporation into the growing strand during sequencing by synthesis. There can be multiple passes of different sets of probes before the substrate is stripped of all detectable labels, or before the detectable label or reversible terminator is removed from an incorporated nucleotide during sequencing. In general, if four nucleotides are used during a pass, a cycle will only consist of a single pass for standard four nucleotide sequencing by synthesis.

As used herein, an image refers to an image of a field taken during a cycle or a pass within a cycle. In some embodiments, a single image is limited to detection of a single color of a detectable label.

As used herein, the term "field" refers to a single region of a substrate that is imaged. During a typical assay a single field is imaged at least once per cycle. For example, for a 20 cycle assay, with 4 colors, there can be 20*4=80 images, all of the same field.

A "target analyte" or "analyte" refers to a single molecule, compound, complex, substance or component that is to be identified, quantified, and otherwise characterized. A target analyte can comprise by way of example, but not limitation to, a single molecule (of any molecular size), a single biomolecule, a polypeptide, a protein (folded or unfolded), a polynucleotide molecule (RNA, cDNA, or DNA), a fragment thereof, a modified molecule thereof, such as a modified nucleic acid, or a combination thereof. In an embodiment, a target polynucleotide comprises a hybridized primer to facilitate sequencing by synthesis. The target analytes are recognized by probes, which can be used to sequence, identify, and quantify the target analytes using optical detection methods described herein.

A "probe" as used herein refers to a molecule that is capable of binding to other molecules (e.g., a complementary labelled nucleotide during sequencing by synthesis, polynucleotides, polypeptides or full-length proteins, etc.), cellular components or structures (lipids, cell walls, etc.), or cells for detecting or assessing the properties of the molecules, cellular components or structures, or cells. The probe comprises a structure or component that binds to the target analyte. In some embodiments, multiple probes may recognize different parts of the same target analyte. Examples of probes include, but are not limited to, a labelled reversible terminator nucleotide, an aptamer, an antibody, a polypeptide, an oligonucleotide (DNA, RNA), or any combination thereof. Antibodies, aptamers, oligonucleotide sequences and combinations thereof as probes are also described in detail below.

The probe can comprise a detectable label that is used to detect the binding of the probe to a target analyte. The probe can be directly or indirectly bound to, hybridized to, conjugated to, or covalently linked to the target analyte.

As used herein, the term detectable label refers to a molecule bound to a probe that is capable of generating a detectable optical signal when the probe is bound to a target analyte and imaged using an optical imaging system. The detectable label can be directly or indirectly bound to, hybridized to, conjugated to, or covalently linked to the probe. In some embodiments, the detectable label is a fluorescent molecule or a chemiluminescent molecule. The probe can be detected optically via the detectable label.

As used herein, the term optical distribution model refers to a statistical distribution of probabilities for light detection from a point source. These include, for example, a Gaussian distribution. The Gaussian distribution can be modified to include anticipated aberrations in detection to generate a point spread function as an optical distribution model.

Overview

Provided herein are systems and methods that facilitate optical detection and discrimination of probes bound to tightly packed analytes bound to the surface of a substrate. In part, the methods and systems described herein rely on repeated detection of a plurality of target analytes on the surface of a substrate to improve the accuracy of identification of a relative location of each analyte on the substrate. This information can then be used to perform signal deconvolution on each image of a field of the substrate for each cycle to reliably identify a signal from a probe bound to the target analyte. In some embodiments, this type of deconvolution processing can be used to distinguish between different probes bound to the target analyte that have overlapping emission spectrum when activated by an activating light. In some embodiments, the deconvolution processing can be used to separate optical signals from neighboring analytes. This is especially useful for substrates with analytes having a density wherein optical detection is challenging due to the diffraction limit of optical systems.

In some embodiments, the methods and systems described herein are particularly useful in sequencing. By providing methods and systems that facilitate reliable optical detection on densely packed substrates, costs associated with sequencing, such as reagents, number of clonal molecules used, processing and read time, can all be reduced to greatly advance sequencing technologies, specifically, single molecule sequencing by synthesis using optically detected nucleotides.

Although the systems and methods described herein have important implications for advancing sequencing technology, the methods and systems described herein are generally applicable to optical detection of analytes bound to the surface of a substrate, especially on the single molecule level.

Sequencing Cost Reduction

Sequencing technologies include image based systems developed by companies such as Illumina and Complete Genomics and electrical based systems developed by companies such as Ion Torrent and Oxford Nanopore. Image based sequencing systems currently have the lowest sequencing costs of all existing sequencing technologies. Image based systems achieve low cost through the combination of high throughput imaging optics and low cost consumables. However, prior art optical detection systems have minimum center-to-center spacing between adjacent resolvable molecules at about a micron, in part due to the diffraction limit of optical systems. In some embodiments, described herein are methods for attaining significantly lower costs for an image based sequencing system using existing biochemistries using cycled detection, determination of precise positons of analytes, and use of the positional information for highly accurate deconvolution of imaged signals to accommodate increased packing densities that operate below the diffraction limit.

Provided herein are systems and methods to facilitate imaging of signals from analytes immobilized on a surface with a center-to-center spacing below the diffraction limit. These systems and methods use advanced imaging systems to generate high resolution images, and cycled detection to facilitate positional determination of molecules on the substrate with high accuracy and deconvolution of images to obtain signal identity for each molecule on a densely packed surface with high accuracy. These methods and systems allow single molecule sequencing by synthesis on a densely packed substrate to provide highly efficient and very high throughput polynucleotide sequence determination with high accuracy.

The major cost components for sequencing systems are primarily the consumables which include biochip and reagents and secondarily the instrument costs. To reach a $10 30× genome, a 100 fold cost reduction, the amount of data per unit area needs to increase by 100 fold and the amount of reagent per data point needs to drop by 100 fold.

FIG. 1 shows sequencer throughput versus array pitch and outlines a system design which meets the criteria needed for a $10 genome. The basic idea is that to achieve a 100 fold cost reduction, the amount of data per unit area needs to increase by 100 fold and the amount of reagent per data point needs to drop by 100 fold. To achieve these reduction in costs, provided herein are methods and systems that facilitate reliable sequencing of polynucleotides immobilized on the surface of a substrate at a density below the diffraction limit. These high density arrays allow more efficient usage of reagents and increase the amount of data per unit area. In addition, the increase in the reliability of detection allows for a decrease in the number of clonal copies that must be synthesized to identify and correct errors in sequencing and detection, further reducing reagent costs and data processing costs.

High Density Distributions of Analytes on a Surface of a Substrate

FIG. 2A shows a proposed embodiment of a high-density region of 80 nm diameter binding regions (spots) on a 240 nm pitch. In this embodiment, an ordered array can be used where single-stranded DNA molecule exclusively binds to specified regions on chip. In some embodiments, concatemers (i.e., a long continuous DNA molecule that contains multiple copies of the same DNA sequence linked in series) smaller than 40 kB are used so as to not overfill the spot. The size of the concatemers scales roughly with area, meaning the projected length of the smaller concatemer will be approximate 4 kB to 5 kB resulting in approximately 10 copies if the same amplification process is used. It is also possible to use 4 kB lengths of DNA and sequence single molecules directly. Another option is to bind a shorter segment of DNA with unsequenced filler DNA to bring the total length up to the size needed to create an exclusionary molecule.

Figure 2B:
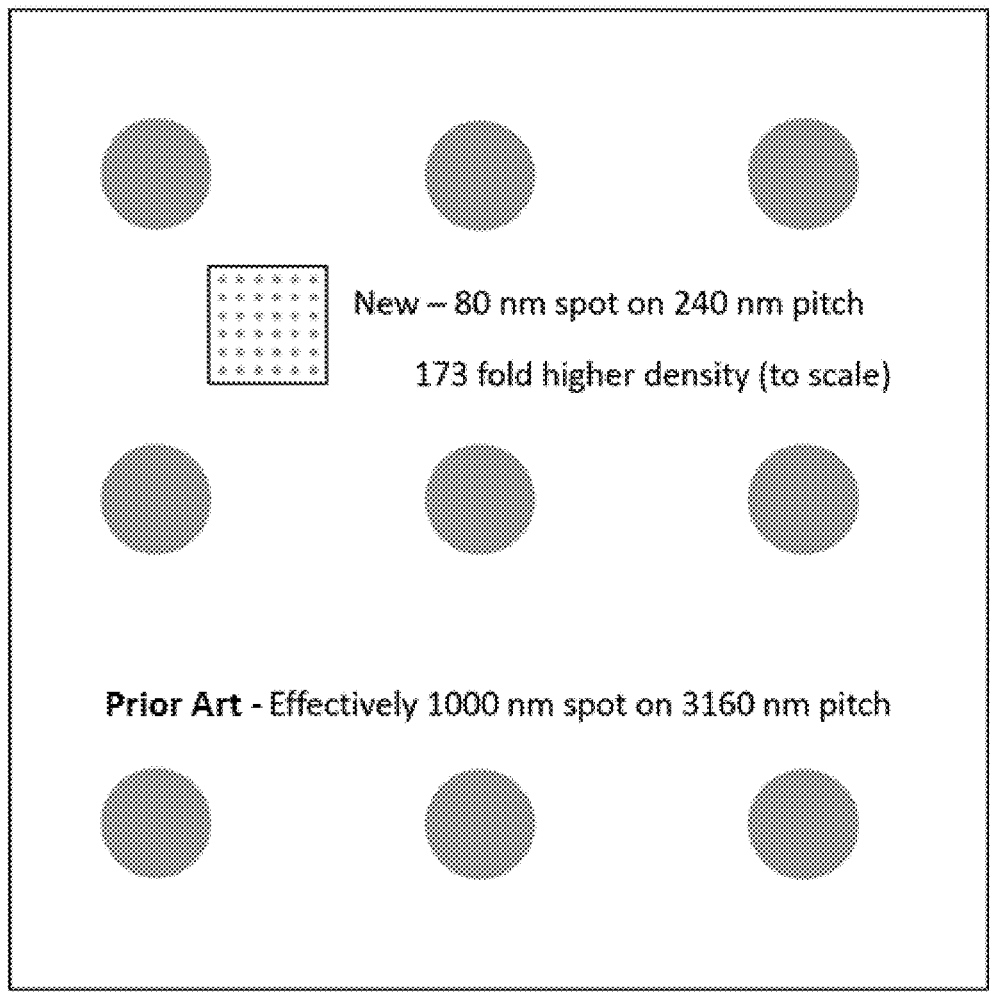
FIG. 2B is a comparison of the proposed substrate density compared to a sample effective density used for a $1,000 genome.

FIG. 2B is a comparison of the proposed pitch compared to a sample effective pitch used for a $1,000 genome. The density of the new array is 170 fold higher, meeting the criteria of achieving 100 fold higher density. The number of copies per imaging spot per unit area also meets the criteria of being at least 100 fold lower than the prior existing platform. This helps ensure that the reagent costs are 100 fold more cost effective than baseline.

Imaging Densely Packed Single Biomolecules and the Diffraction Limit

The primary constraint for increased molecular density for an imaging platform is the diffraction limit. The equation for the diffraction limit of an optical system is:

$$D = \frac{\lambda}{2NA}$$

where D is the diffraction limit, $\lambda$ is the wavelength of light, and NA is the numerical aperture of the optical system. Typical air imaging systems have NA's of 0.6 to 0.8. Using $\lambda$=600 nm, the diffraction limit is between 375 nm and 500 nm. For a water immersion system, the NA is ~1.0, giving a diffraction limit of 300 nm.

If features on an array or other substrate surface comprising biomolecules are too close, two optical signals will overlap so substantially so you just see a single blob that cannot be reliably resolved based on the image alone. This can be exacerbated by errors introduced by the optical imaging system, such as blur due to inaccurate tracking of a moving substrate, or optical variations in the light path between the sensor and the surface of a substrate.

The transmitted light or fluorescence emission wavefronts emanating from a point in the specimen plane of the microscope become diffracted at the edges of the objective aperture, effectively spreading the wavefronts to produce an image of the point source that is broadened into a diffraction pattern having a central disk of finite, but larger size than the original point. Therefore, due to diffraction of light, the image of a specimen never perfectly represents the real details present in the specimen because there is a lower limit below which the microscope optical system cannot resolve structural details.

The observation of sub-wavelength structures with microscopes is difficult because of the diffraction limit. A point object in a microscope, such as a fluorescent protein or nucleotide single molecule, generates an image at the intermediate plane that consists of a diffraction pattern created by the action of interference. When highly magnified, the diffraction pattern of the point object is observed to consist of a central spot (diffraction disk) surrounded by a series of diffraction rings. Combined, this point source diffraction pattern is referred to as an Airy disk.

The size of the central spot in the Airy pattern is related to the wavelength of light and the aperture angle of the objective. For a microscope objective, the aperture angle is described by the numerical aperture (NA), which includes the term sin θ, the half angle over which the objective can gather light from the specimen. In terms of resolution, the radius of the diffraction Airy disk in the lateral (x,y) image plane is defined by the following formula: Abbe Resolution$_{x,y}$=λ/2 NA, where λ is the average wavelength of illumination in transmitted light or the excitation wavelength band in fluorescence. The objective numerical aperture (NA=n·sin(θ)) is defined by the refractive index of the imaging medium (n; usually air, water, glycerin, or oil) multiplied by the sine of the aperture angle (sin(θ)). As a result of this relationship, the size of the spot created by a point source decreases with decreasing wavelength and increasing numerical aperture, but always remains a disk of finite diameter. The Abbe resolution (i.e., Abbe limit) is also referred to herein as the diffraction limit and defines the resolution limit of the optical system.

If the distance between the two Airy disks or point-spread functions is greater than this value, the two point sources are considered to be resolved (and can readily be distinguished). Otherwise, the Airy disks merge together and are considered not to be resolved.

Thus, light emitted from a single molecule detectable label point source with wavelength λ, traveling in a medium with refractive index n and converging to a spot with half-angle θ will make a diffraction limited spot with a diameter: d=λ/2*NA. Considering green light around 500 nm and a NA (Numerical Aperture) of 1, the diffraction limit is roughly d=λ/2=250 nm (0.25 μm), which limits the density of analytes such as single molecule proteins and nucleotides on a surface able to be imaged by conventional imaging techniques. Even in cases where an optical microscope is equipped with the highest available quality of lens elements, is perfectly aligned, and has the highest numerical aperture, the resolution remains limited to approximately half the wavelength of light in the best case scenario. To increase the resolution, shorter wavelengths can be used such as UV and X-ray microscopes. These techniques offer better resolution but are expensive, suffer from lack of contrast in biological samples and may damage the sample.

Deconvolution

Deconvolution is an algorithm-based process used to reverse the effects of convolution on recorded data. The concept of deconvolution is widely used in the techniques of signal processing and image processing. Because these techniques are in turn widely used in many scientific and engineering disciplines, deconvolution finds many applications.

In optics and imaging, the term "deconvolution" is specifically used to refer to the process of reversing the optical distortion that takes place in an optical microscope, electron microscope, telescope, or other imaging instrument, thus creating clearer images. It is usually done in the digital domain by a software algorithm, as part of a suite of microscope image processing techniques.

The usual method is to assume that the optical path through the instrument is optically perfect, convolved with a point spread function (PSF), that is, a mathematical function that describes the distortion in terms of the pathway a theoretical point source of light (or other waves) takes through the instrument. Usually, such a point source contributes a small area of fuzziness to the final image. If this function can be determined, it is then a matter of computing its inverse or complementary function, and convolving the acquired image with that. Deconvolution maps to division in the Fourier co-domain. This allows deconvolution to be easily applied with experimental data that are subject to a Fourier transform. An example is NMR spectroscopy where the data are recorded in the time domain, but analyzed in the frequency domain. Division of the time-domain data by an exponential function has the effect of reducing the width of Lorenzian lines in the frequency domain. The result is the original, undistorted image.

However, for diffraction limited imaging, deconvolution is also needed to further refine the signals to improve resolution beyond the diffraction limit, even if the point spread function is perfectly known. It is very hard to separate two objects reliably at distances smaller than the Nyquist distance. However, described herein are methods and systems using cycled detection, analyte position determination, alignment, and deconvolution to reliably detect objects separated by distances much smaller than the Nyquist distance.

Sequencing

Optical detection imaging systems are diffraction-limited, and thus have a theoretical maximum resolution of ~300 nm with fluorophores typically used in sequencing. To date, the best sequencing Systems have had center-to-center spacings between adjacent polynucleotides of ~600 nm on their arrays, or ~2× the diffraction limit. This factor of 2X is needed to account for intensity, array & biology variations that can result in errors in position. In order to achieve a $10 genome, an approximately 200 nm center to center spacing is required, which requires sub-diffraction-limited imaging capability.

For sequencing, the purpose of the system and methods described herein are to resolve polynucleotides that are sequenced on a substrate with a center-to-center spacing below the diffraction limit of the optical system.

As described herein, we provide methods and systems to achieve sub-diffraction-limited imaging in part by identifying a position of each analyte with a high accuracy (e.g., 10 nm RMS or less). By comparison, state of the art Super Resolution systems (Harvard/STORM) can only identify location with an accuracy down to 20 nm RMS, 2× worse than this system. Thus, the methods and system disclosed herein enable sub-diffraction limited-imaging to identify densely-packed molecules on a substrate to achieve a high data rate per unit of enzyme, data rate per unit of time, and high data accuracy to achieve a $10 genome. These sub-diffraction limited imaging techniques are broadly applicable to techniques using cycled detection as described herein.

Imaging and Cycled Detection

As described herein, each of the detection methods and systems required cycled detection to achieve sub-diffraction limited imaging. Cycled detection includes the binding and imaging or probes, such as antibodies or nucleotides, bound to detectable labels that are capable of emitting a visible light optical signal. By using positional information from a series of images of a field from different cycles, deconvolution to resolve signals from densely packed substrates can be used effectively to identify individual optical signals from signals obscured due to the diffraction limit of optical imaging. After multiple cycles the precise location of the molecule will become increasingly more accurate. Using this information additional calculations can be performed to aid in crosstalk correction regarding known asymmetries in the crosstalk matrix occurring due to pixel discretization effects.

Methods and systems using cycled probe binding and optical detection are described in U.S. Publication No. 2015/0330974, Digital Analysis of Molecular Analytes Using Single Molecule Detection, published Nov. 19, 2015, incorporated herein by reference in its entirety.

In some embodiments, the raw images are obtained using sampling that is at least at the Nyquist limit to facilitate more accurate determination of the oversampled image. Increasing the number of pixels used to represent the image by sampling in excess of the Nyquist limit (oversampling) increases the pixel data available for image processing and display.

Theoretically, a bandwidth-limited signal can be perfectly reconstructed if sampled at the Nyquist rate or above it. The Nyquist rate is defined as twice the highest frequency component in the signal. Oversampling improves resolution, reduces noise and helps avoid aliasing and phase distortion by relaxing anti-aliasing filter performance requirements. A signal is said to be oversampled by a factor of N if it is sampled at N times the Nyquist rate.

Thus, in some embodiments, each image is taken with a pixel size no more than half the wavelength of light being observed. In some embodiments, a pixel size of 162.5 nm×162.5 nm is used in detection to achieve sampling at or above the Nyquist limit. Sampling at a frequency of at least the Nyquist limit during raw imaging of the substrate is preferred to optimize the resolution of the system or methods described herein. This can be done in conjunction with the deconvolution methods and optical systems described herein to resolve features on a substrate below the diffraction limit with high accuracy.

Processing Images from Different Cycles

There are several barriers overcome by the present invention to achieve sub-diffraction limited imaging.

Pixelation error is present in raw images and prevents identification of information present from the optical signals due to pixelation. Sampling at least at the Nyquist frequency and generation of an oversampled image as described herein each assist in overcoming pixelation error.

The point-spread (PSF) of various molecules overlap because the PSF size is greater than the pixel size (below Nyquist) and because the center-to-center spacing is so small that crosstalk due to spatial overlap occurs. Nearest neighbor variable regression (for center-to center crosstalk) can be used to help with deconvolution of multiple overlapping optical signals. But this can be improved if we know the relative location of each analyte on the substrate and have good alignment of images of a field.

After multiple cycles the precise location of the molecule will become increasingly more accurate. Using this information additional calculations can be performed to aid in deconvolution by correcting for known asymmetries in the spatial overlap of optical signals occurring due to pixel discretization effects and the diffraction limit. They can also be used to correct for overlap in emission spectrum from different emission spectrum.

Highly accurate relative positional information for each analyte can be achieved by overlaying images of the same field from different cycles to generate a distribution of measured peaks from optical signals of different probes bound to each analyte. This distribution can then be used to generate a peak signal that corresponds to a single relative location of the analyte. Images from a subset of cycles can be used to generate relative location information for each analyte. In some embodiments, this relative position information is provided in a localization file.

The specific area imaged for a field for each cycle may vary from cycle to cycle. Thus, to improve the accuracy of identification of analyte position for each image, an alignment between images of a field across multiple cycles can be performed. From this alignment, offset information compared to a reference file can then be identified and incorporated into the deconvolution algorithms to further increase the accuracy of deconvolution and signal identification for optical signals obscured due to the diffraction limit. In some embodiments, this information is provided in a Field Alignment File.

Signal Detection (Cross-Talk/Nearest Neighbor)

Once relative positional information is accurately determined for analytes on a substrate and field images from each cycle are aligned with this positional information, analysis of each oversampled image using crosstalk and nearest neighbor regression can be used to accurately identify an optical signal from each analyte in each image.

In some embodiments, a plurality of optical signals obscured by the diffraction limit of the optical system are identified for each of a plurality of biomolecules immobilized on a substrate and bound to probes comprising a detectable label. In some embodiments, the probes are incorporated nucleotides and the series of cycles is used to determine a sequence of a polynucleotide immobilized on the array using single molecule sequencing by synthesis.

Simulations of Deconvolution Applied to Images

Figure 3:
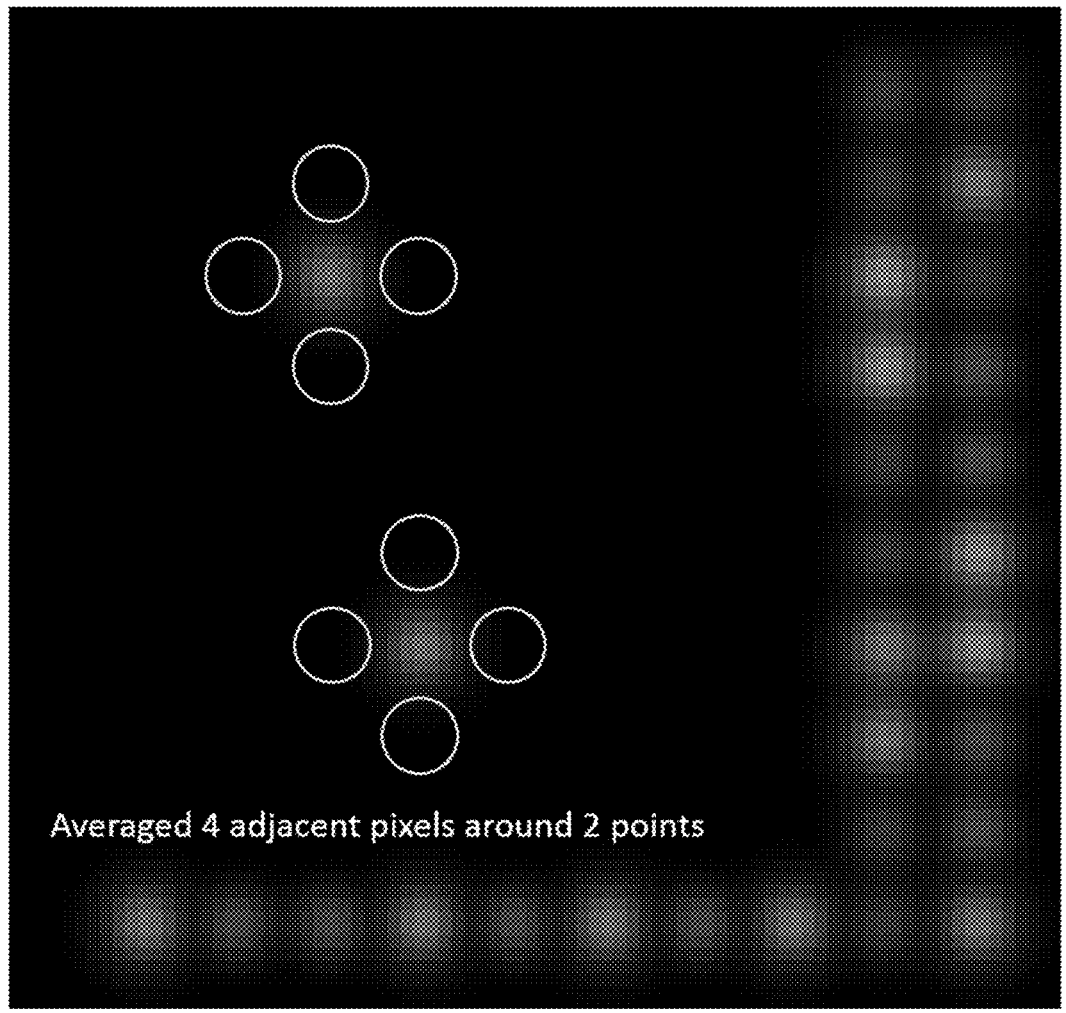
FIG. 3 shows crosstalk calculations for simulated single molecules on a 600 nm pitch processed with a 2× filter.

Molecular densities are limited by crosstalk from neighboring molecules. FIG. 3 depicts simulated images of single molecules. This particular image is a simulation of a single molecule array on a 600 nm pitch that has been processed with a 2× oversampled filter. Crosstalk into eight adjacent spots is averaged as a function of array pitch and algorithm type.

Figure 4:
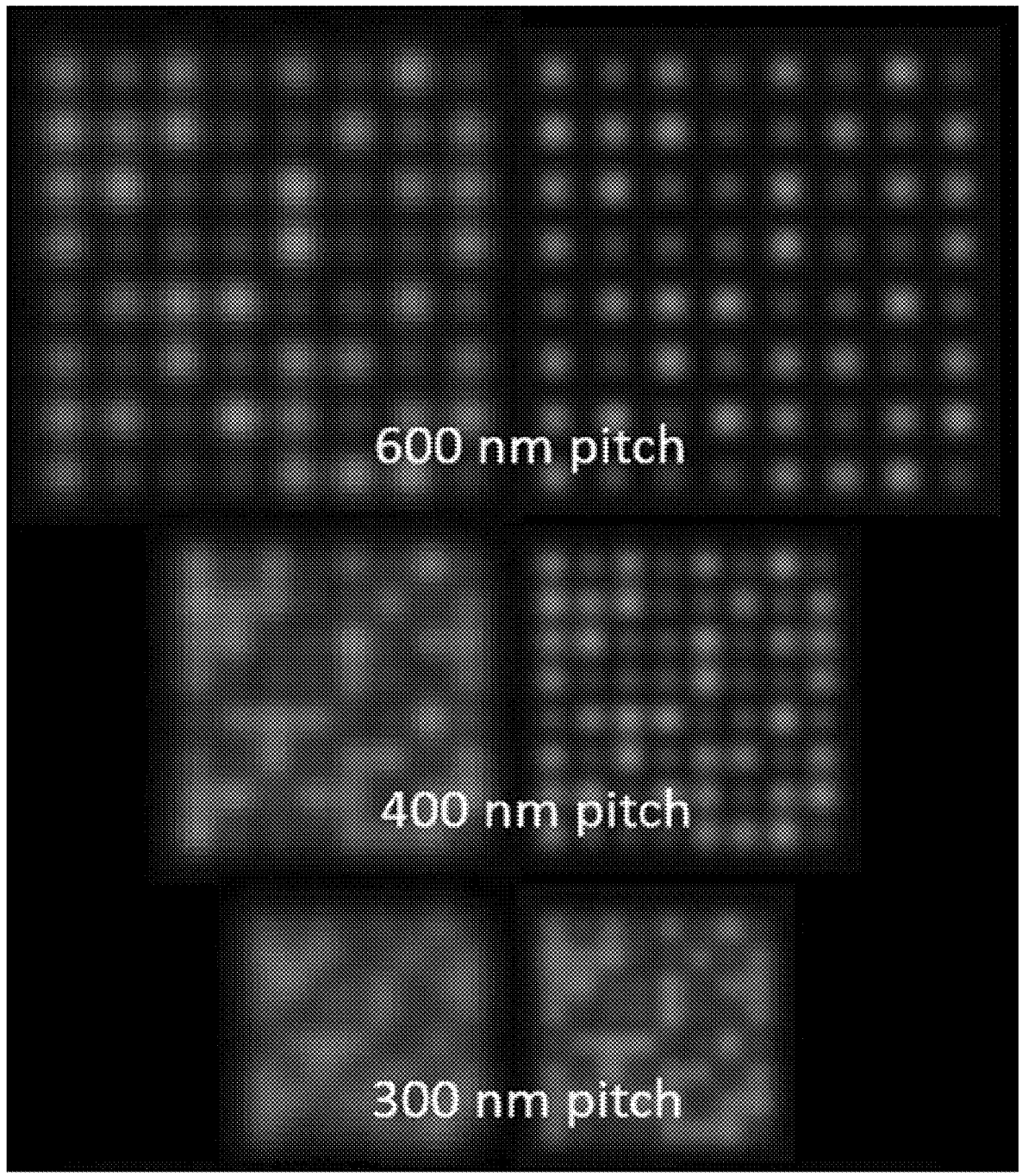
FIG. 4 shows Oversampled 2× (left) vs. Oversampled 4× and Deconvolved (right) simulations of images of detection of single molecule analytes on a substrate at center-to-center distances of 600 nm, 400 nm, and 300 nm.
Figure 5:
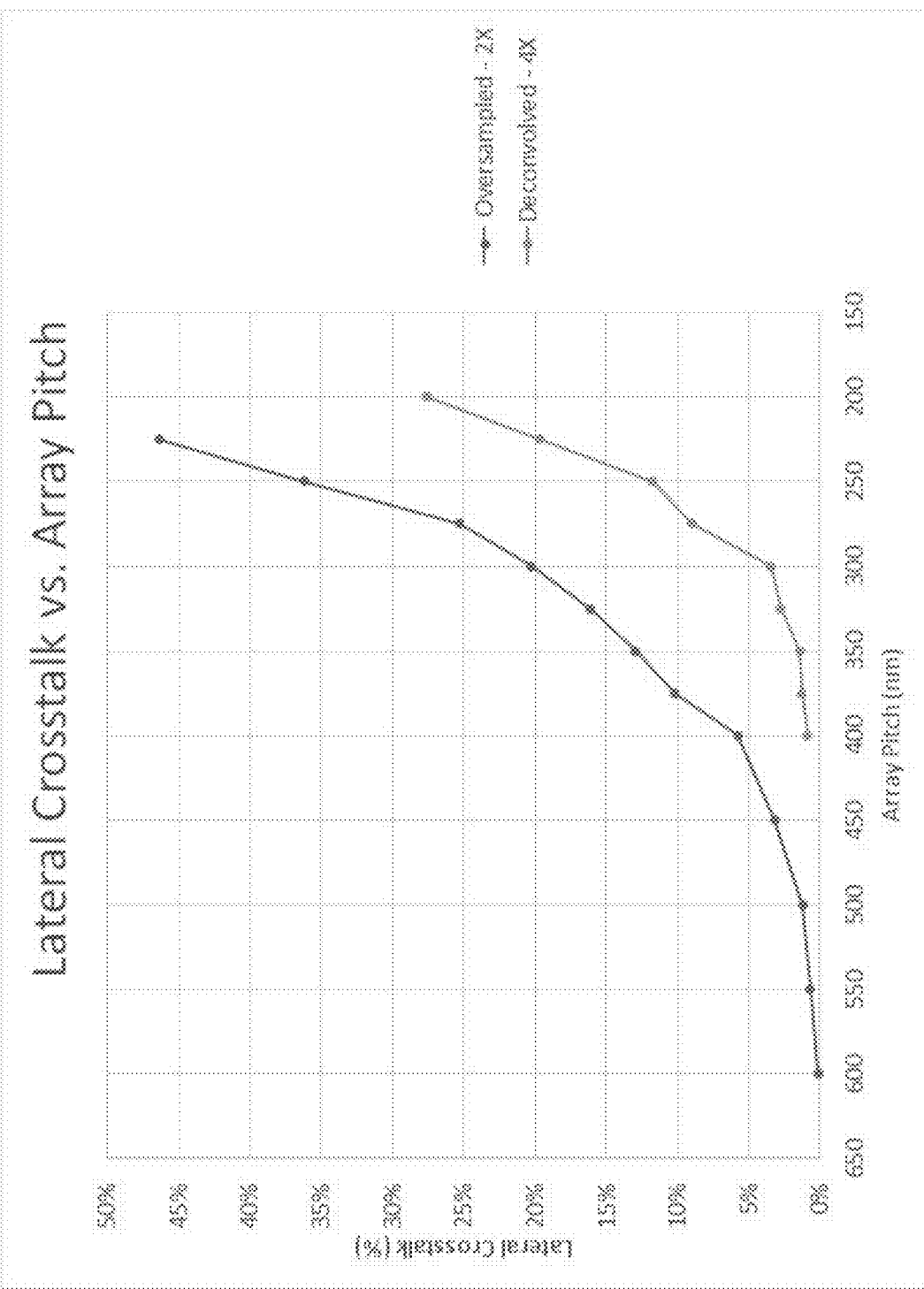
FIG. 5 shows a plot of crosstalk between adjacent spots at different center-to-center distances between single analytes (array pitch (nm)) processed using Oversampled 2× vs. Oversampled 4× and Deconvolved simulations.

FIG. 4 is a series of images processed with multiple pitches and two variations of image processing algorithms, the first is a 2× oversampled image and the second is a 4× oversampled image with deconvolution, as described herein. FIG. 5 is the crosstalk analysis of these two types of image processing at pitches down to 200 nm. Acceptable crosstalk levels at or below 25% with 2× oversample occurs for pitches at or above 275 nm. Acceptable crosstalk levels at or below 25% with 4× deconvolution using the point spread function of the optical system occurs for pitches at or above 210 nm.

The physical size of the molecule will broaden the spot roughly half the size of the binding area. For example, for an 80 nm spot the pitch will be increased by roughly 40 nm. Smaller spot sizes may be used, but this will have the trade-off that fewer copies will be allowed and greater illumination intensity will be required. A single copy provides the simplest sample preparation but requires the greatest illumination intensity.

Methods for sub-diffraction limit imaging discussed to this point involve image processing techniques of oversampling, deconvolution and crosstalk correction. Described herein are methods and systems that incorporate determination of the precise relative location analytes on the substrate using information from multiple cycles of probe optical signal imaging for the analytes. Using this information additional calculations can be performed to aid in crosstalk correction regarding known asymmetries in the crosstalk matrix occurring due to pixel discretization effects.

Methods

Figure 6:
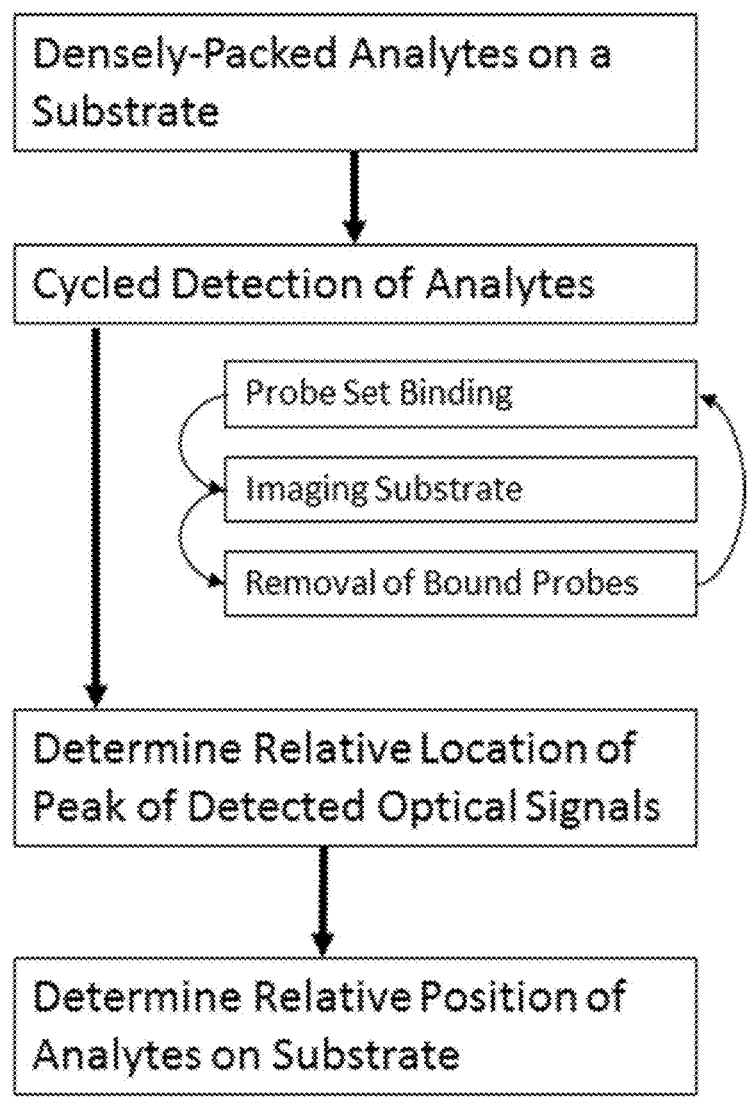
FIG. 6 depicts a flowchart for a method of determining the relative positions of analytes on a substrate with high accuracy, according to an embodiment of the invention.

In some embodiments, as shown in FIG. 6, provided herein is a method for accurately determining a relative position of analytes immobilized on the surface of a densely packed substrate. The method includes first providing a substrate comprising a surface, wherein the surface comprises a plurality of analytes immobilized on the surface at discrete locations. Then, a plurality of cycles of probe binding and signal detection on said surface is performed. Each cycle of detection includes contacting the analytes with a probe set capable of binding to target analytes immobilized on the surface, imaging a field of said surface with an optical system to detect a plurality of optical signals from individual probes bound to said analytes at discrete locations on said surface, and removing bound probes if another cycle of detection is to be performed. From each image, a peak location from each of said plurality of optical signals from images of said field from at least two of said plurality of cycles is detected. The location of peaks for each analyte is overlaid, generating a cluster of peaks from which an accurate relative location of each analyte on the substrate is then determined.

Figure 7:
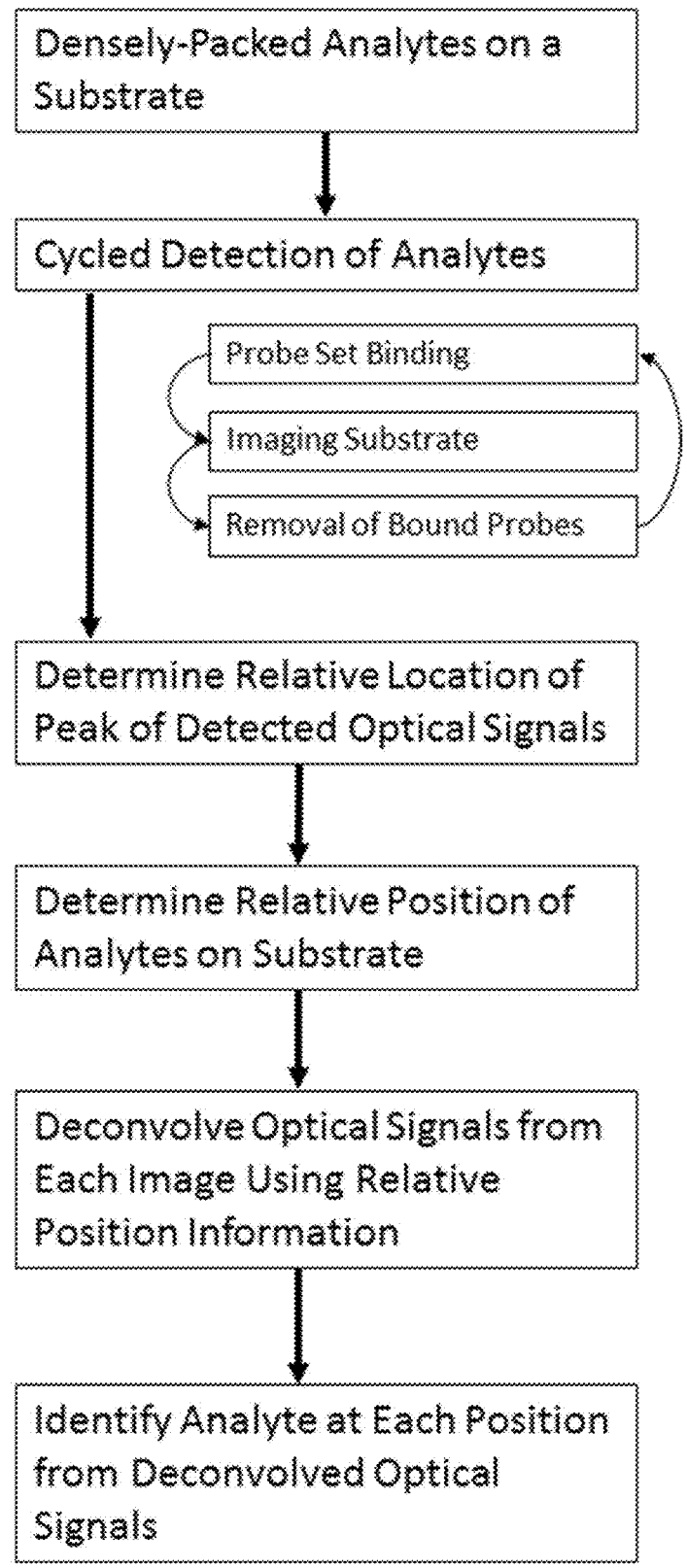
FIG. 7 depicts a flowchart for a method of identifying individual analytes from deconvolved optical signals detected from a substrate, according to an embodiment of the invention.

In some embodiments, as shown in FIG. 7, the accurate position information for analytes on the substrate is then used in a deconvolution algorithm incorporating position information (e.g., for identifying center-to-center spacing between neighboring analytes on the substrate) can be applied to the image to deconvolve overlapping optical signals from each of said images. In some embodiments, the deconvolution algorithm includes nearest neighbor variable regression for spatial discrimination between neighboring analytes with overlapping optical signals.

Figure 8:
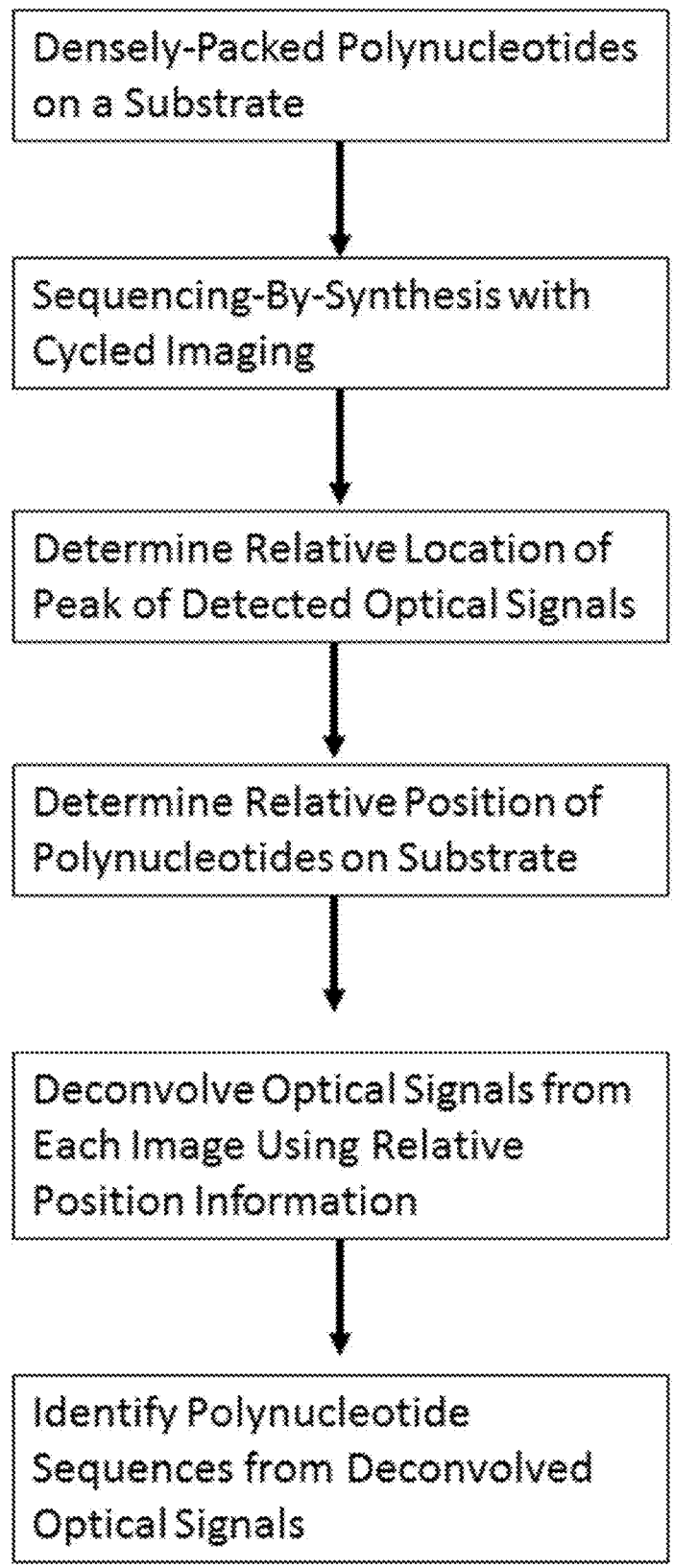
FIG. 8 depicts a flowchart for a method of sequencing polynucleotides immobilized on a substrate, according to an embodiment of the invention.

In some embodiments, as shown in FIG. 8, the method of analyte detection is applied for sequencing of individual polynucleotides immobilized on a substrate.

Figure 9:
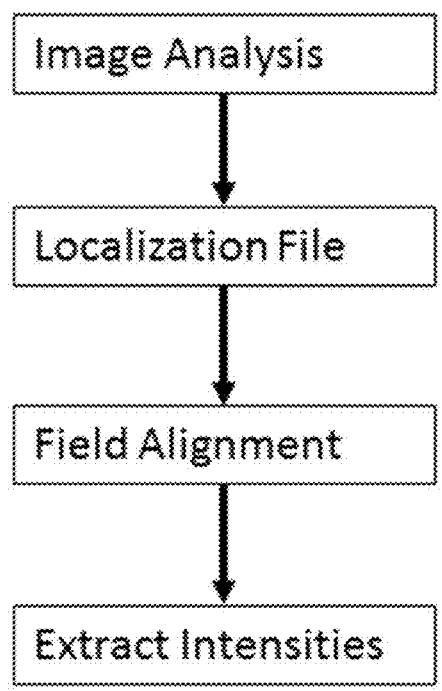
FIG. 9 shows an overview of steps in an optical signal detection process from cycled detection, according to an embodiment of the invention.
Figure 11:
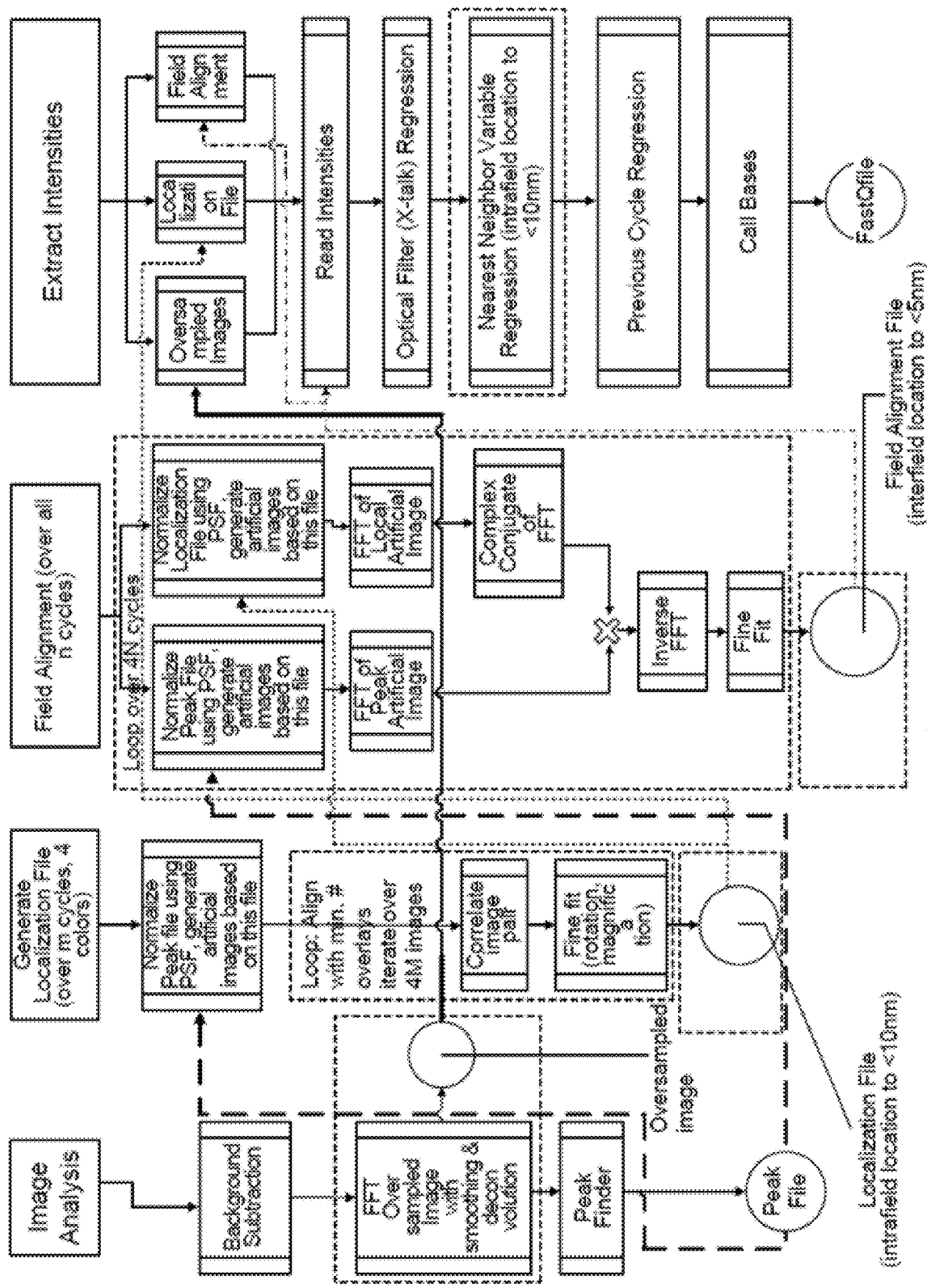
FIG. 11 depicts a detailed flowchart of steps for an optical signal detection and deconvolution process for images from cycled detection of a densely-packed substrate, according to an embodiment of the invention.

In some embodiments, optical signals are deconvolved from densely packed substrates as shown in FIG. 11. The steps can be divided into four different sections as shown in FIG. 9: 1) Image Analysis, which includes generation of oversampled images from each image of a field for each cycle, and generation of a peak file (i.e., a data set) including peak location and intensity for each detected optical signal in an image. 2) Generation of a Localization File, which includes alignment of multiple peaks generated from the multiple cycles of optical signal detection for each analyte to determining an accurate relative location of the analyte on the substrate. 3) Generation of a Field Alignment file, which includes offset information for each image to align images of the field from different cycles of detection with respect to a selected reference image. 4) Extract Intensities, which uses the offset information and location information in conjunction with deconvolution modeling to determine an accurate identity of signals detected from each oversampled image. The "Extract Intensities" step can also include other error correction, such as previous cycle regression used to correct for errors in sequencing by synthesis processing and detection. The steps performed in each section are described in further detail below.

Figures 10A, 10B:
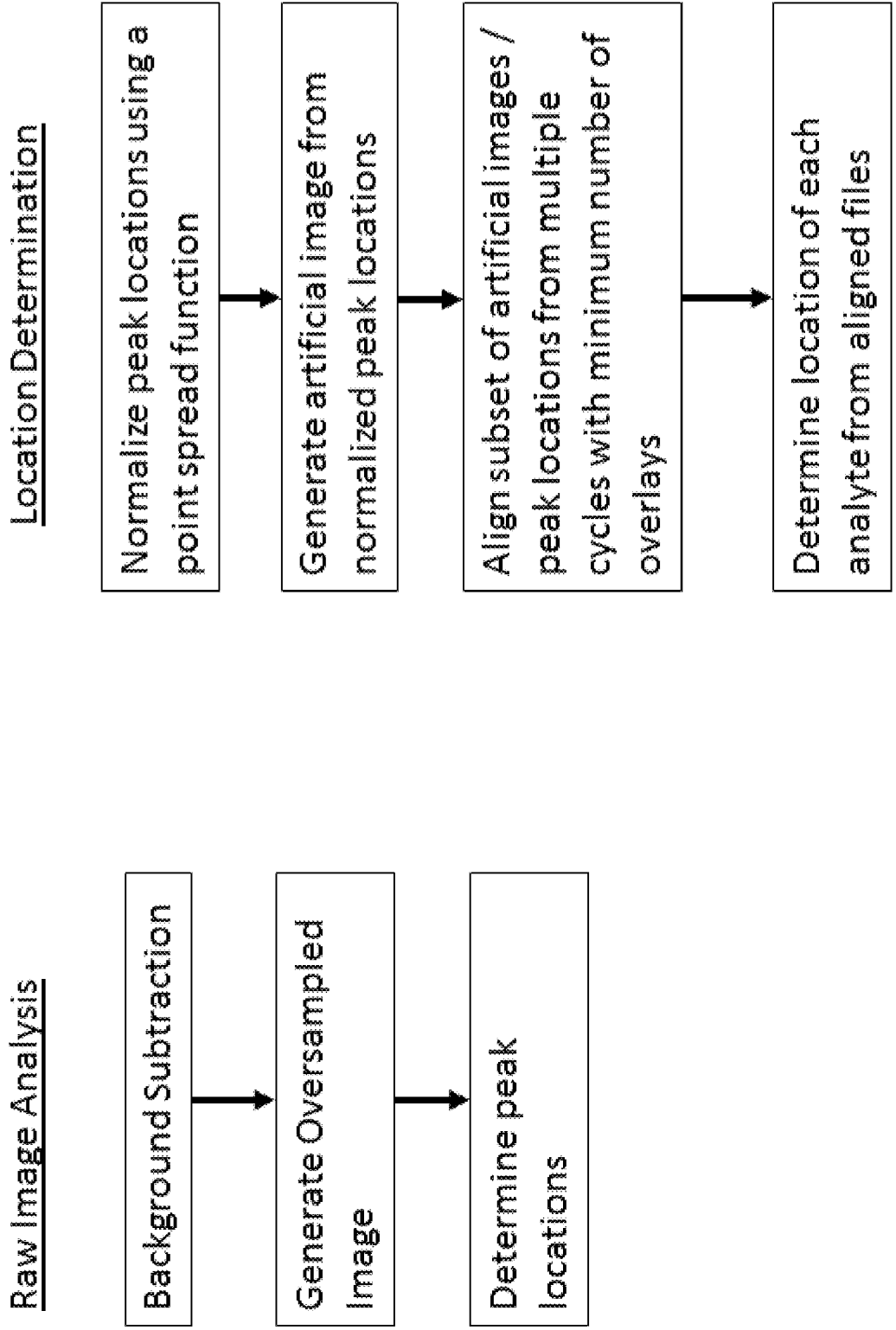
FIG. 10A shows a flowchart of steps for initial raw image analysis, according to an embodiment of the invention.
FIG. 10B shows a flowchart of steps for location determination from optical signal peak information from a plurality of cycles, according to an embodiment of the invention.

Under the image analysis steps shown in FIG. 10A and FIG. 11, the images of each field from each cycle are processed to increase the number of pixels for each detected signal, sharpen the peaks for each signal, and identify peak intensities form each signal. This information is used to generate a peak file for each field for each cycle that includes a measure of the position of each analyte (from the peak of the observed optical signal), and the intensity, from the peak intensity from each signal. In some embodiments, the image from each field first undergoes background subtraction to perform an initial removal of noise from the image. Then, the images are processed using smoothing and deconvolution to generate an oversampled image, which includes artificially generated pixels based on modeling of the signal observed in each image. In some embodiments, the oversampled image can generate 4 pixels, 9 pixels, or 16 pixels from each pixel from the raw image.

Peaks from optical signals detected in each raw image or present in the oversampled image are then identified and intensity and position information for each detected analyte is placed into a peak file for further processing.

In some embodiments, N raw images corresponding to all images detected from each cycle and each field of a substrate or output into N oversampled images and N peak files for each imaged field. The peak file comprises a relative position of each detected analyte for each image. In some embodiments, the peak file also comprises intensity information for each detected analyte. In some embodiments, one peak file is generated for each color and each field in each cycle. In some embodiments, each cycle further comprises multiple passes, such that one peak file can be generated for each color and each field for each pass in each cycle. In some embodiments, the peak file specifies peak locations from optical signals within a single field.

In preferred embodiments, the peak file includes XY position information from each processed oversampled image of a field for each cycle. The XY position information comprises estimated coordinates of the locations of each detected detectable label from a probe (such as a fluorophore) from the oversampled image. The peak file can also include intensity information from the signal from each individual detectable label.

Generation of an oversampled image is used to overcome pixelation error to identify information present that cannot be extracted due to pixelation. Initial processing of the raw image by smoothing and deconvolution helps to provide more accurate information in the peak files so that the position of each analyte can be determined with higher accuracy, and this information subsequently can be used to provide a more accurate determination of signals obscured in diffraction limited imaging.

In some embodiments, the raw images are obtained using sampling that is at least at the Nyquist limit to facilitate more accurate determination of the oversampled image. Increasing the number of pixels used to represent the image by sampling in excess of the Nyquist limit (oversampling) increases the pixel data available for image processing and display.

Theoretically, a bandwidth-limited signal can be perfectly reconstructed if sampled at the Nyquist rate or above it. The Nyquist rate is defined as twice the highest frequency component in the signal. Oversampling improves resolution, reduces noise and helps avoid aliasing and phase distortion by relaxing anti-aliasing filter performance requirements. A signal is said to be oversampled by a factor of N if it is sampled at N times the Nyquist rate.

Thus, in some embodiments, each image is taken with a pixel size no more than half the wavelength of light being observed. In some embodiments, a pixel size of 162.5 nm×162.5 nm is used in detection to achieve sampling at or above the Nyquist limit.

Smoothing uses an approximating function capture important patterns in the data, while leaving out noise or other fine-scale structures/rapid phenomena. In smoothing, the data points of a signal are modified so individual points are reduced, and points that are lower than the adjacent points are increased leading to a smoother signal. Smoothing is used herein to smooth the diffraction limited optical signal detected in each image to better identify peaks and intensities from the signal.

Although each raw image is diffraction limited, described herein are methods that result in collection of multiple signals from the same analyte from different cycles. An embodiment of this method is shown in the flowchart in FIG. 10B. These multiple signals from each analyte are used to determine a position much more accurate than the diffraction limited signal from each individual image. They can be used to identify molecules within a field at a resolution of less than 5 nm. This information is then stored as a localization file, as shown in FIG. 11. The highly accurate position information can then be used to greatly improve signal identification from each individual field image in combination with deconvolution algorithms, such as cross-talk regression and nearest neighbor variable regression.

As shown in FIG. 11, the steps for generating a localization file use the location information provided in the peak files to determine relative positions of a set of analytes on the substrate. In some embodiments, each localization file contains relative positions from sets of analytes from a single imaged field of the substrate. The localization file combines position information from multiple cycles to generate highly accurate position information for detected analytes below the diffraction limit.

In some embodiments, the relative position information for each analyte is determined on average to less than a 10 nm standard deviation (i.e., RMS, or root mean square). In some embodiments, the relative position information for each analyte is determined on average to less than a 10 nm 2× standard deviation. In some embodiments, the relative position information for each analyte is determined on average to less than a 10 nm 3× standard deviation. In some embodiments, the relative position information for each analyte is determined to less than a 10 nm median standard deviation. In some embodiments, the relative position information for each analyte is determined to less than a 10 nm median 2× standard deviation. In some embodiments, the relative position information for each analyte is determined to less than a 10 nm median 3× standard deviation.

From a subset of peak files for a field from different cycles, a localization file is generated to determine a location of analytes on the array. As shown in FIG. 11, in some embodiments, a peak file is first normalized using a point spread function to account for aberrations in the optical system. The normalized peak file can be used to generate an artificial normalized image based on the location and intensity information provided in the peak file. Each image is then aligned. In some embodiments, the alignment can be performed by correlating each image pair and performing a fine fit. Once aligned, position information for each analyte from each cycle can then be overlaid to provide a distribution of position measurements on the substrate. This distribution is used to determine a single peak position that provides a highly accurate relative position of the analyte on the substrate. In some embodiments, a Poisson distribution is applied to the overlaid positions for each analyte to determine a single peak.

The peaks determined from at least a subset of position information from the cycles are then recorded in a localization file, which comprises a measure of the relative position of each detected analyte with an accuracy below the diffraction limit. As described, images from only subset of cycles are needed to determine this information.

As shown in FIG. 11, a normalized peak file from each field for each cycle and color and the normalized localization file can be used to generate offset information for each image from a field relative to a reference image of the field. This offset information can be used to improve the accuracy of the relative position determination of the analyte in each raw image for further improvements in signal identification from a densely packed substrate and a diffraction limited image. In some embodiments, this offset information is stored as a field alignment file. In some embodiments, the position information of each analyte in a field from the combined localization file and field alignment file is less than 10 nm RMS, less than 5 nm RMS, or less than 2 nm RMS.

In some embodiments, a field alignment file is generated by alignment of images from a single field by determining offset information relative to a master file from the field. One field alignment file is generated for each field. This file is generated from all images of the field from all cycles, and includes offset information for all images of the field relative to a reference image from the field.

In some embodiments, before alignment, each peak file is normalized with a point spread function, followed by generation of an artificial image from the normalized peak file and Fourier transform of the artificial image. The Fourier transform of the artificial image of the normalized peak file is then convolved with a complex conjugate of the Fourier transform of an artificial image from the normalized localization file for the corresponding field. This is done for each peak file for each cycle. The resulting files then undergo an inverse Fourier transform to regenerate image files, and the image files are aligned relative to the reference file from the field to generate offset information for each image file. In some embodiments, this alignment includes a fine fit relative to a reference file.

The field alignment file thus contains offset information for each oversampled image, and can be used in conjunction with the localization file for the corresponding field to generate highly accurate relative position for each analyte for use in the subsequent "Extract Intensities" steps.

As an example where 20 cycles are performed on a field, and one image is generated for each of 4 colors to be detected, thus generating 80 images of the field, one Field Alignment file is generated for all 80 images (20 cycles*4 colors) taken of the field. In some embodiments, the field alignment file contents include: the field, the color observed for each image, the step type in the cycled detection (e.g., binding or stripping), and the image offset coordinates relative to the reference image.

In some embodiments, during the alignment process XY "shifts" or "residuals" needed to align 2 images are calculated, and the process is repeated for remaining images, best fit residual to apply to all is calculated.

Figure 10C:
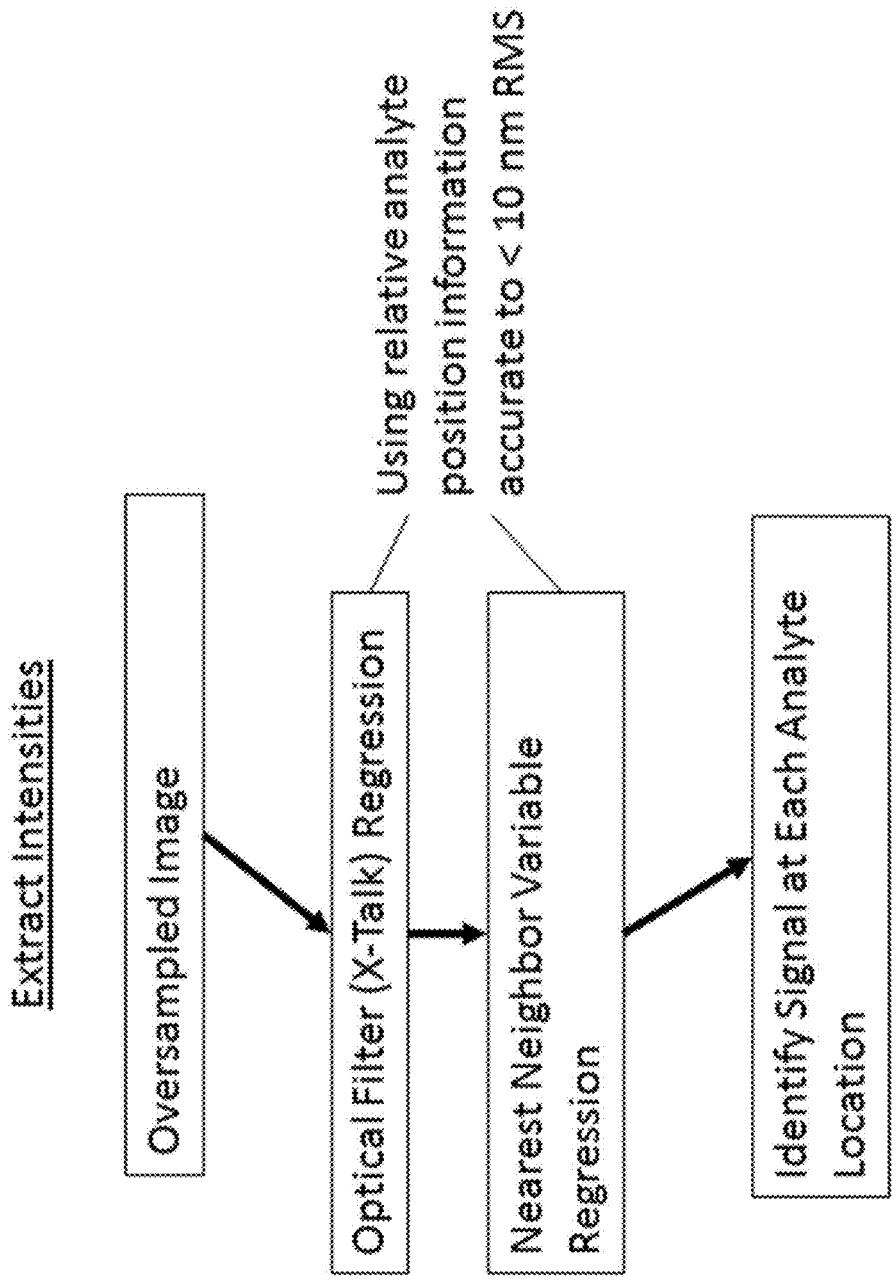
FIG. 10C shows a flowchart of steps for identification of overlapping optical signals from an image using accurate relative positional information and image deconvolution algorithms, according to an embodiment of the invention.

In some embodiments, residuals that exceed a threshold are thrown out, and best fit is re-calculated. This process is repeated until all individual residuals are within the threshold Each oversampled image is then deconvolved using the accurate position information from the localization file and the offset information from the field alignment file. An embodiment of the intensity extraction step is shown in FIG. 10C and FIG. 11. The Point Spread Function (PSF) of various molecules overlap because the center-to-center spacing is so small that the point-spread function of signals from adjacent analytes overlaps. Nearest neighbor variable regression in combination with the accurate analyte position information and/or offset information can be used to deconvolve signals from adjacent analytes that have a center-to-center distance that inhibits resolution due to the diffraction limit. The use of the accurate relative position information for each analyte facilitates spatial deconvolution of optical signals from neighboring analytes below the diffraction limit. In some embodiments, the relative position of neighboring analytes is used to determine an accurate center-to-center distance between neighboring analytes, which can be used in combination with the point spread function of the optical system to estimate spatial cross-talk between neighboring analytes for use in deconvolution of the signal from each individual image. This enables the use of substrates with a density of analytes below the diffraction limit for optical detection techniques, such as polynucleotide sequencing.

In certain embodiments, emission spectra overlap between different signals (i.e. "cross-talk"). For example, during sequencing by synthesis, the four dyes used in the sequencing process typically have some overlap in emission spectra.

In particular embodiments, a problem of assigning a color (for example, a base call) to different features in a set of images obtained for a cycle when cross talk occurs between different color channels and when the cross talk is different for different sets of images can be solved by cross-talk regression in combination with the localization and field alignment files for each oversampled image to remove overlapping emission spectrums from optical signals from each different detectable label used. This further increases the accuracy of identification of the detectable label identity for each probe bound to each analyte on the substrate.

Thus, in some embodiments, identification of a signal and/or its intensity from a single image of a field from a cycle as disclosed herein uses the following features: 1) Oversampled Image—provides intensities and signals at defined locations. 2) Accurate Relative Location—Localization File (provides location information from information from at least a subset of cycles) and Field Alignment File (provides offset/alignment information for all images in a field). 3) Image Processing—Nearest Neighbor Variable Regression (spatial deconvolution) and Cross-talk regression (emission spectra deconvolution) using accurate relative position information for each analyte in a field. Accurate identification of probes (e.g., antibodies for detection or complementary nucleotides for sequencing) for each analyte.

Image Processing Simulations

The effects of the methods and systems disclosed herein are illustrated in simulated cross-talk plots shown in FIG. 12A, FIG. 12B, FIG. 13A and FIG. 13B. For each of these figures, a cross-talk plot showing the intensity of emission spectrum correlated with one of four fluorophores at each detected analyte in a 10 um×10 um region is shown. Each axis corresponding to one of the four fluorophores extends to each corner of the plot. Thus, a spot located in the center of the plot will have equal contribution of intensity from all four fluorophores. Emission intensity detected from an individual fluorophore during an imaging cycle is assigned to move the spot in a direction either towards X, Y; X, −Y; −X, Y; or −X, −Y. Thus, separation of populations of spots along these four axes indicates a clear deconvolved signal from a fluorophore at an analyte location. Each simulation is based on detection of 1024 molecules in a 10.075 um×10.075 um region, indicating a density of 10.088 molecules per micron squared, or an average center-to-center distance between molecules of about 315 nm. This is correlated with an imaging region of about 62×62 pixels at a pixel size of 162.5 nm×162.5 nm.

Figure 12B:
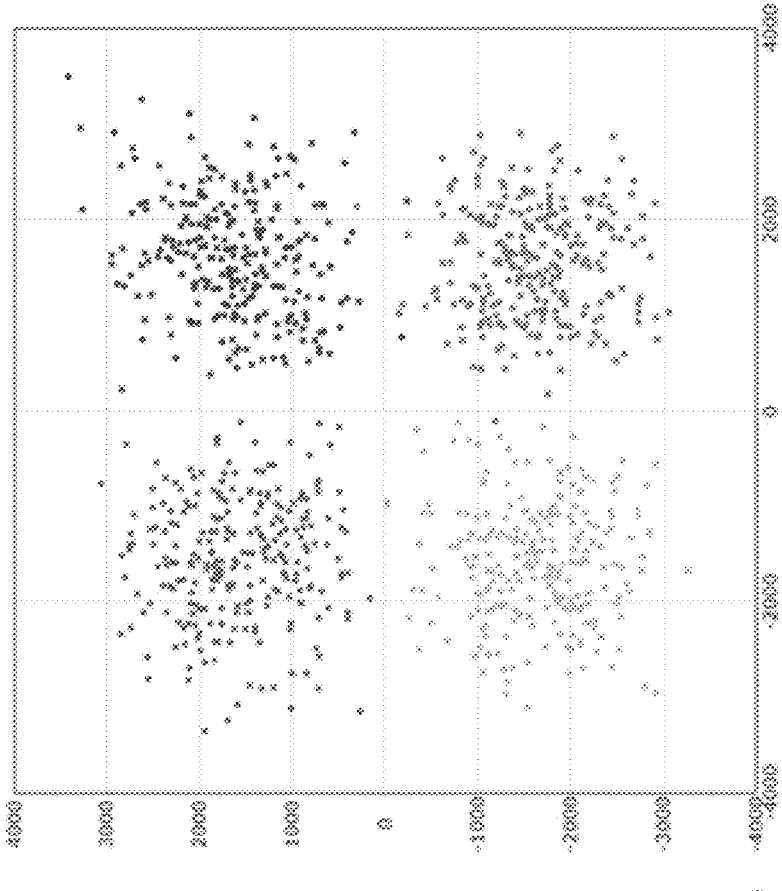
FIG. 12B shows a cross-talk plot of fluorophore intensity between four fluorophores from a 4× oversampled image.
Figure 12A:
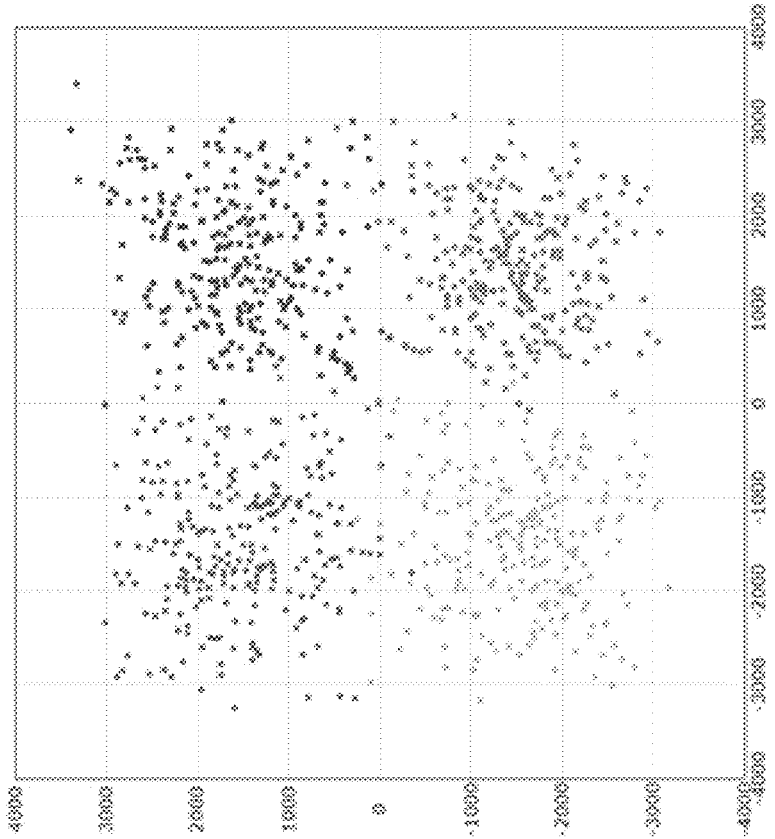
FIG. 12A shows a cross-talk plot of fluorophore intensity between four fluorophores from optical signals detected from the raw image.
Figure 13B:
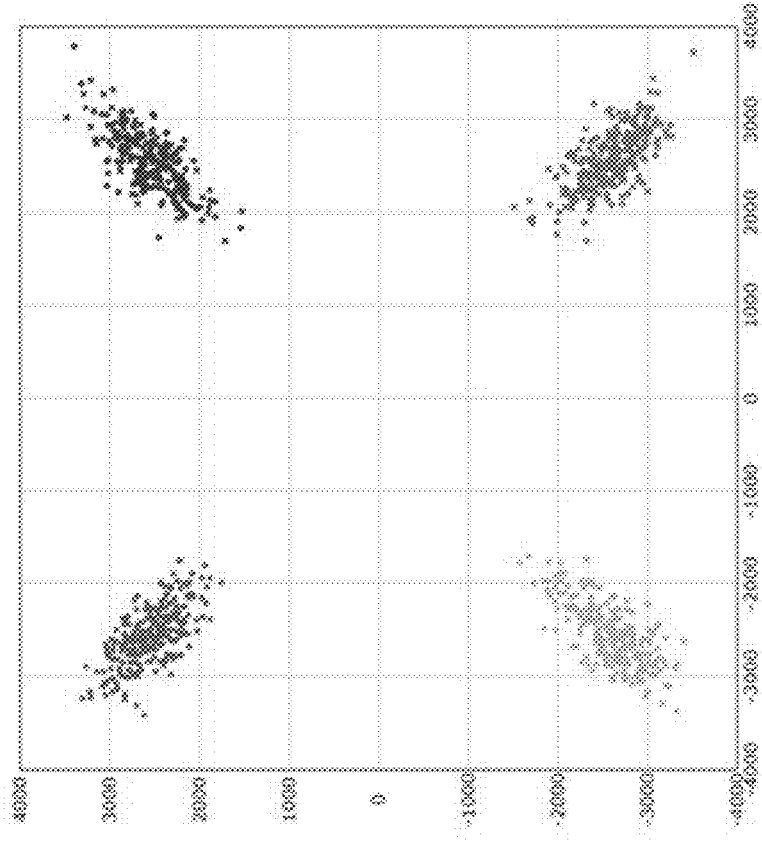
FIG. 13B shows a cross-talk plot of fluorophore intensity between four fluorophores from a 4× oversampled and deconvolved image using a deconvolution algorithm with accurate analyte position information, according to an embodiment of the invention.
Figure 13A:
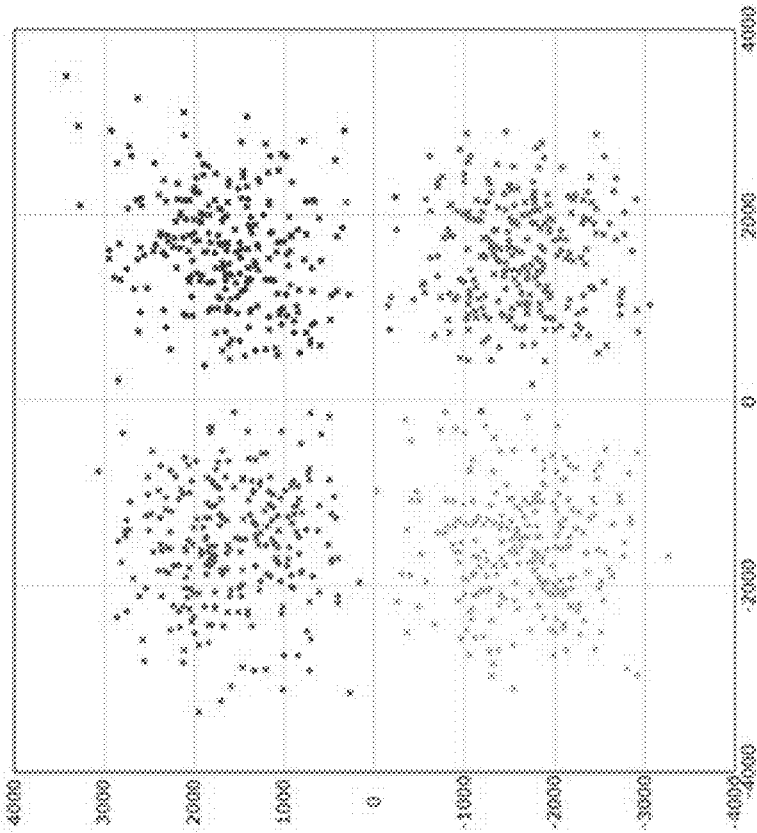
FIG. 13A shows a cross-talk plot of fluorophore intensity between four fluorophores from a 4× oversampled image.

FIG. 12A shows the cross-talk plot of fluorophore intensity between the four fluorophores from optical signals detected from the raw image. FIG. 12B and FIG. 13A each shows the separation between the four fluorophores achieved by generating a 4× oversampled image, indicating the achievement of some removal of cross-talk at each analyte. FIG. 13B shows a cross-talk plot for the same imaging region but with deconvolution and nearest neighbor regression performed as shown in FIG. 11 and described herein. As compared with FIG. 13A and FIG. 12A, each analyte detected shows clear separation of its optical signal from the other fluorophores, indicating a highly accurate fluorophore identification for each analyte.

Figure 14B:
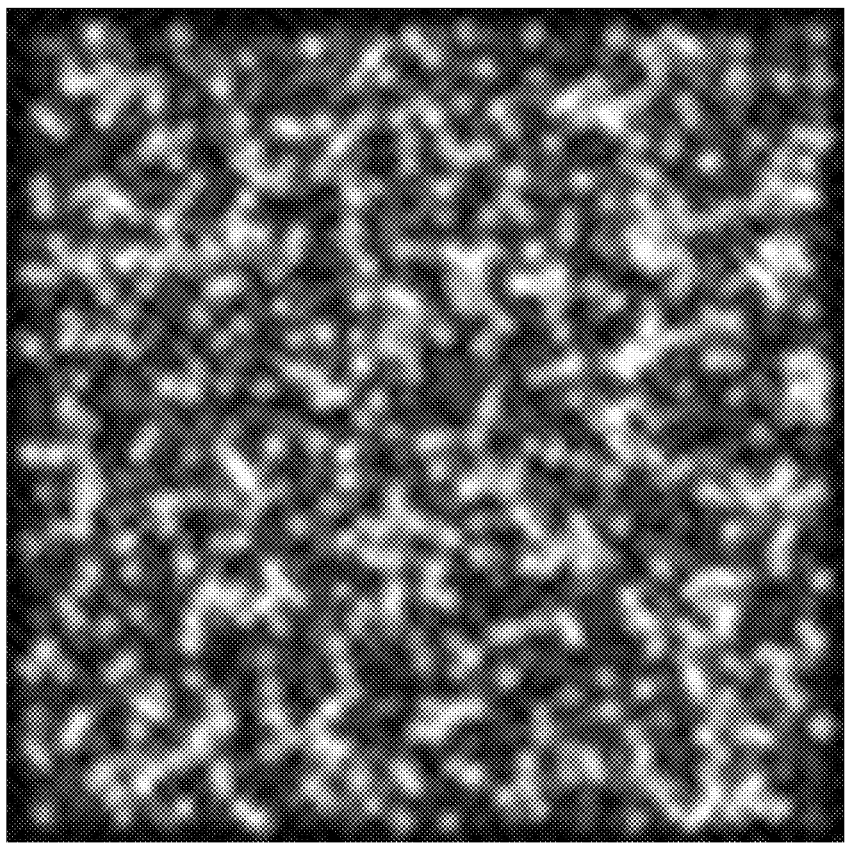
FIG. 14B shows a simulated four-color composite of a deconvolved image at a center-to-center spacing between analytes of about 315 nm.
Figure 14A:
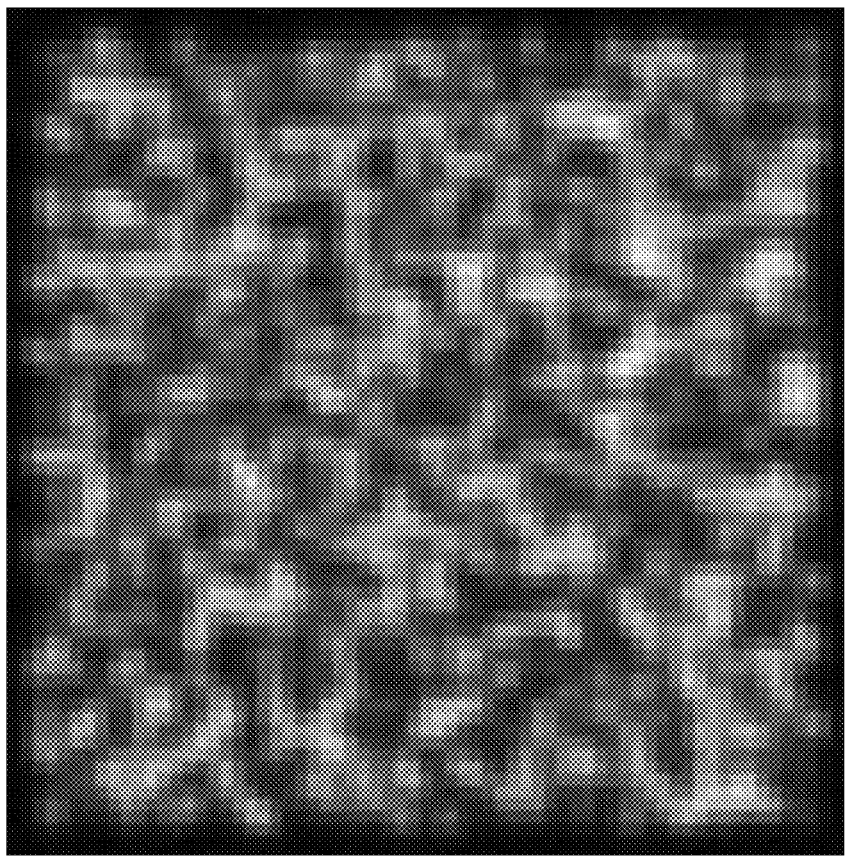
FIG. 14A shows a simulated four-color composite of a raw image of a field at a center-to-center spacing between analytes of about 315 nm.

FIG. 14A and FIG. 14B show a simulated four-color composite of each detected 10.075 µm×10.075 µm region as simulated above. This visually represents the clarity between analytes form the raw image (FIG. 14A) and the image processed as described herein (FIG. 14B).

Sequencing

The methods described above and in FIG. 11 also facilitate sequencing by sequencing by synthesis using optical detection of complementary reversible terminators incorporated into a growing complementary strand on a substrate comprising densely packed polynucleotides. Thus, signals correlating with the sequence of neighboring polynucleotides at a center-to-center distance below the diffraction limit can be reliably detected using the methods and optical detection systems described herein. Image processing during sequencing can also include previous cycle regression based on clonal sequences repeated on the substrate or on the basis of the data itself to correct for errors in the sequencing reaction or detection. In some embodiments, the polynucleotides immobilized on the substrate for sequencing are concatemers. A concatemer can comprise multiple identical copies of a polynucleotide to be sequenced. Thus, each optical signal identified by the methods and systems described herein can refer to a single detectable label (e.g., a fluorophore) from an incorporated nucleotide, or can refer to multiple detectable labels bound to multiple locations on a single concatemer, such that the signal is an average from multiple locations. The resolution that must occur is not between individual detectable labels, but between different concatemers immobilized to the substrate.

In some embodiments, molecules to be sequenced, single or multiple copies, will be bound to the surface using covalent linkages, by hybridizing to capture oligonucleotide on the surface, or by other non-covalent binding. The bound molecules will remain on the surface for hundreds of cycles and can be re-interrogated with different primer sets, following stripping of the initial sequencing primers, to confirm the presence of specific variants.

In one embodiment, the fluorophores and blocking groups may be removed using chemical reactions.

In another embodiment, the fluorescent and blocking groups may be removed using UV light.

In one embodiment, the molecules to be sequenced could be immobilized on reactive surfaces that have 50-100 nM diameters and these areas would be spaced at a pitch of 150-300 nM. These molecules may have barcodes, attached onto them for target deconvolution and a sequencing primer binding region for initiating sequencing. Buffers will contain appropriate amounts of DNA polymerase to enable an extension reaction. These sited could contain 10-100 copies of the target to be sequenced generated by any of the gene amplification methods available (PCR, whole genome amplification etc.)

In another embodiment, single target molecules, tagged with a barcode and a primer annealing site would be immobilized on a 20-50 nM diameter reactive surface spaced with a pitch of 60-150 nM. The molecules would be sequenced individually.

In one embodiment, a primer would bind to the target and would be extended using one dNTP at a time with a single or multiple fluorophore(s); the surface would be imaged, the fluorophore would be removed and washed and the process repeated to generate a second extension. The presence of multiple fluorophores on the same dNTP will enable defining the number of repeats nucleotides present in some regions of the genome (2 to 5 or more).

In a different embodiment, following primer annealing, all four dNTPs with fluorophores and blocked 3' hydroxyl groups would be used in the polymerase extension reaction, the surface would be imaged and the fluorophore and blocking groups removed and the process repeated for multiple cycles.

In another embodiment, the sequences could be inferred based on ligation reactions that anneal specific probes that ligate based on the presence of a specific nucleotides at a given position.

A random array may be used which will have improved densities over prior art random arrays using the techniques outlined above, however random arrays generally have 4× to 10× reduced areal densities of ordered arrays. Advantages of a random array include a uniform, non-patterned surface for the chip and the use of shorter nucleic acid strands because there is no need to rely on the exclusionary properties of longer strands.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1: Dense Arrays

Methods below will describe how to utilize a square ordered array where the pitch ranges between 200 nm and 333 nm. Additional methods will be described that allow even smaller pitches. An imaging system is described in International Application PCT/US2018/020737, filed Mar. 2, 2018 and incorporated herein by reference, which will be used as a reference system which enables sub-diffraction limit imaging. The optical system can include multiple 2,048 by 2,048 pixel cameras operating up to 100 Hz frames per second (fps) with field size 332.8 um by 332.8 um. This system is capable of measuring as little as a single fluor at and above 90 fps. Using this system with 1-10 copies (or 1-10 fluorophores) per molecule at 85 fps achieves the necessary throughput to image a 63 mm×63 mm slide in under 15 minutes. Biochemistry cycles and imaging are continuously and simultaneously performed, either by using two chips or by dividing a single chip into at least 2 regions.

Example 2: Single-Molecule Sequencing Using Sequencing by Synthesis

Single-molecule sequencing using sequencing-by-synthesis approach was evaluated on the Apton System. To test the methodology, single-stranded DNA templates with 5' phosphate group were first attached to the chip with a tecarbohydrazide activated silicon surface of the flow cell through EDC (1-Ethyl-3-(3-mplate dimethylaminopropyl)carbodiimide) chemistry. The sequencing primer was the annealed the target immobilized on the surface. The sequencing templates used in our initial studies included synthetic oligonucleotide containing EGFR L858R, EGFR T790M, and BRAF V600E mutations and two cDNA samples reversed transcribed from ERCC 00013 and ERCC 00171 control RNA transcripts. After DNA template immobilization and primer annealing, the flow cell is loaded on the Apton instrument for sequencing reactions, which involves multiple cycles of enzymatic single nucleotide incorporation reaction, imaging to detect fluorescence dye detection, followed by chemical cleavage. Therminator IX DNA Polymerase from NEB was used for single base extension reaction, which is a 9° N™ DNA Polymerase variant with an enhanced ability to incorporate modified dideoxynucleotides. Four dNTPs used in the reaction are labeled with 4 different cleavable fluorescent dyes and blocked at 3'-OH group with a cleavable moiety (dCTP-AF488, dATP-AFCy3, dTTP-TexRed, and dGTP-Cy5 from MyChem). During each sequencing reaction cycle, a single labeled dNTP is incorporated and the reaction is terminated because of the 3'-blocking group on dNTP. After dNTP incorporation, the unincorporated nucleotides are removed from the flow-cell by washing and the incorporated fluorescent dye labeled nucleotide is imaged to identify the base. After the images are captured, the fluorescent dye and blocking moiety are cleaved from the incorporated nucleotide using 100 mM TCEP ((tris(2-carboxyethyl)phosphine), pH9.0), allowing subsequent addition of the next complementary nucleotide in next cycle. This extension, detection and cleavage cycle is then repeated to increase the read length.

Figure 15A:
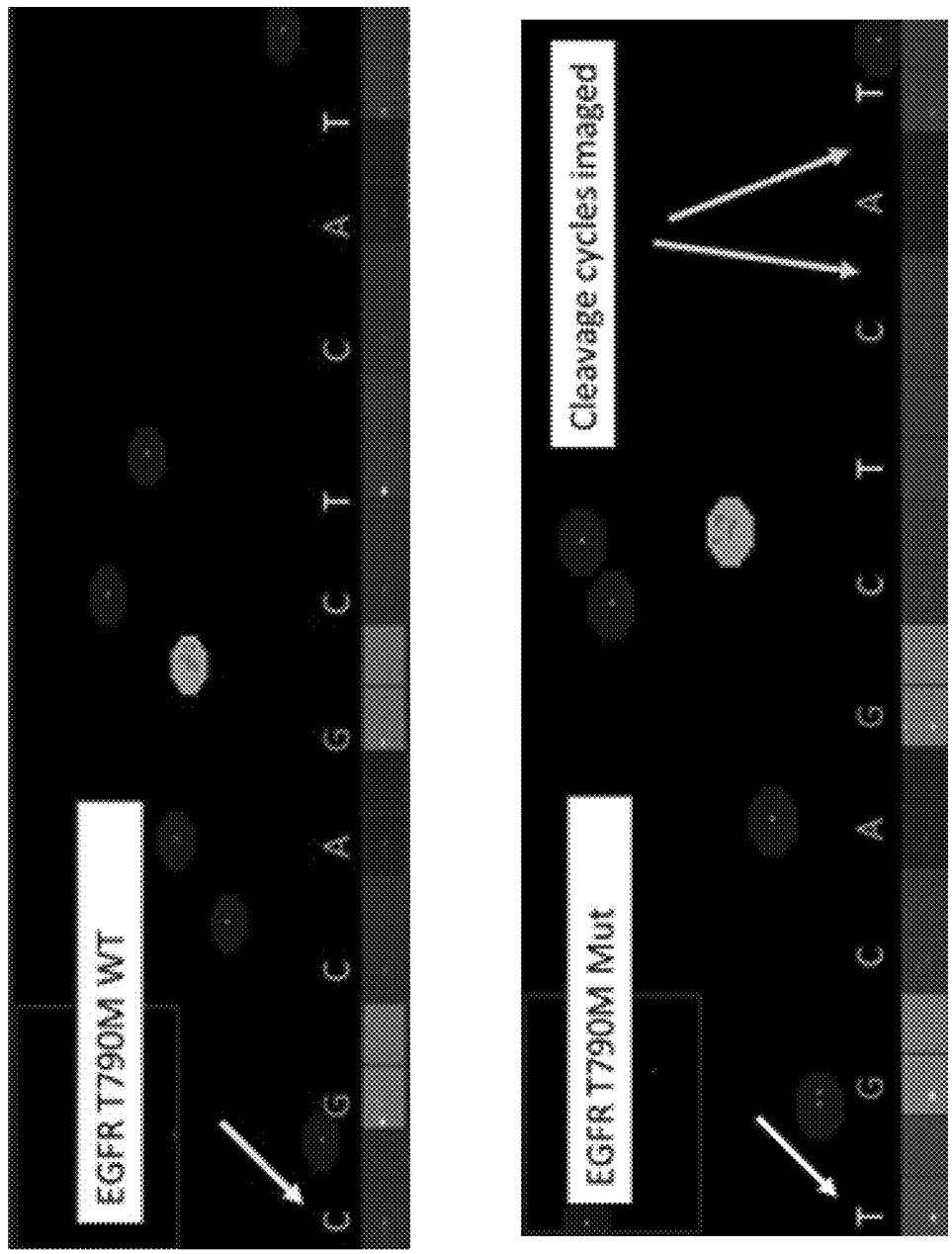
FIG. 15A shows results of sequencing of a 1:1 mixture of synthetic oligonucleotide templates corresponding to the region around codon 790 in the EGFR gene containing equal amounts of mutant and wild type (WT) targets.

FIG. 15A shows results of sequencing of a 1:1 mixture of synthetic oligonucleotide templates corresponding to the region around codon 790 in the EGFR gene containing equal amounts of mutant and wild type (WT) targets. Images from incorporation of dye labeled nucleotides used to sequence synthetic templates corresponding to a region of the EGFR gene near codon 790 with a mutation at the first base (C-incorporation in WT & T-incorporation in mutant) after the primer. The montage in FIG. 15A depicts images from alternating base incorporation and cleavage cycles. This data exhibits the ability of the system to detect 10 cycles of base incorporation. Arrows indicate the base change observed.

The synthetic oligonucleotides used were around 60 nucleotides long. A primer that had a sequence ending one base prior to the mutation in codon 790 was used to enable the extension n reaction. The surface was imaged post incorporation of nucleotides by the DNA polymerase and after the cleavage reaction with TCEP. The yellow circle indicates the location of the template molecule that was aligned using data from 10 consecutive cycles of dye incorporation. Molecules were identified with known color incorporation sequences, following that the actual base incorporations are identified by visual inspections which is labor-intensive.

Figure 15B:
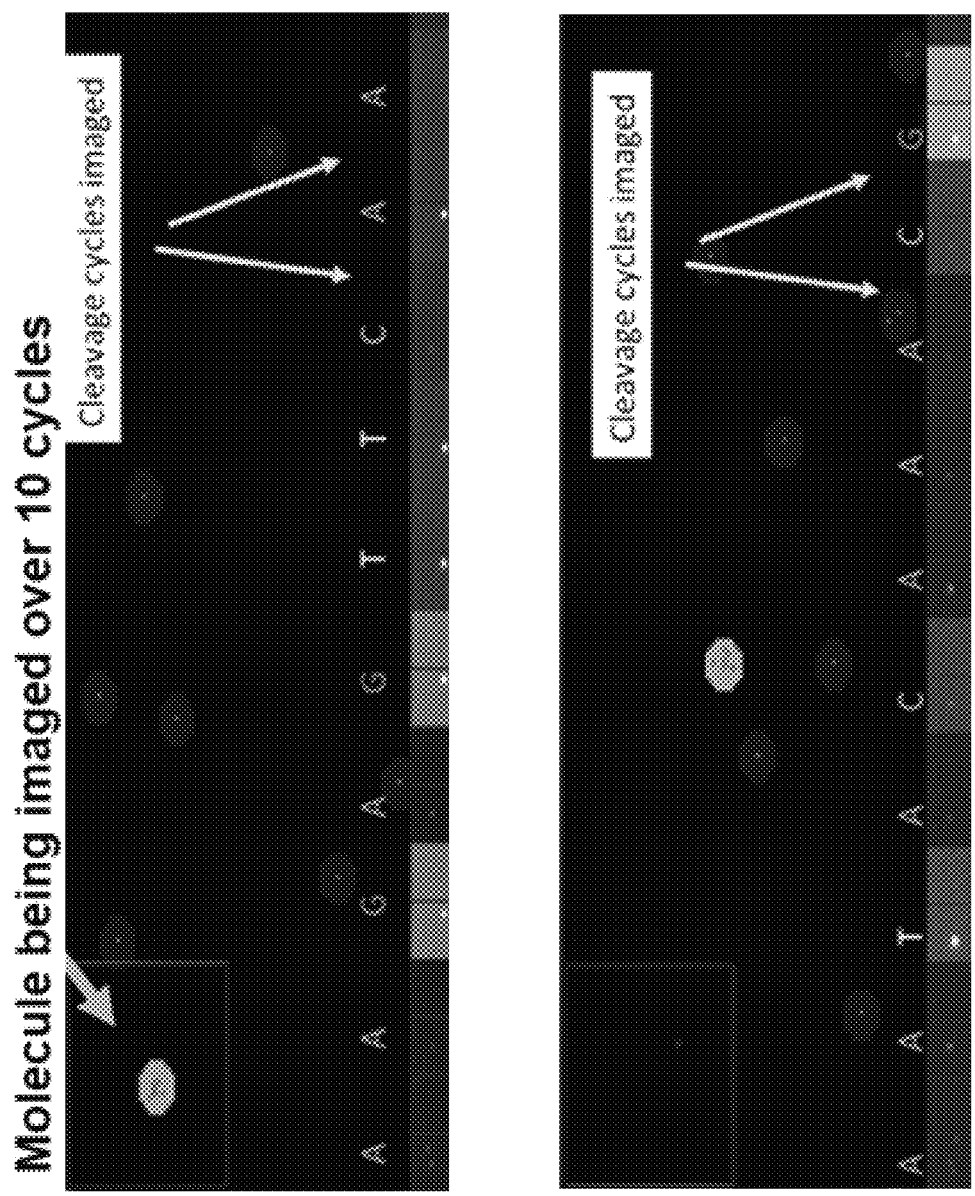
FIG. 15B depicts images from alternating base incorporation and cleavage cycles.

Dye labeled nucleotides were used to sequence cDNA generated from RNA templates. RNA used was generated by T7 transcription from cloned ERCC control plasmids. FIG. 15B depicts images from alternating base incorporation and cleavage cycles. The data exhibits the ability of the system to detect 10 cycles of base incorporation. The sequence observed were correct. Yellow arrows indicate the cleavage cycles.

Figure 16:
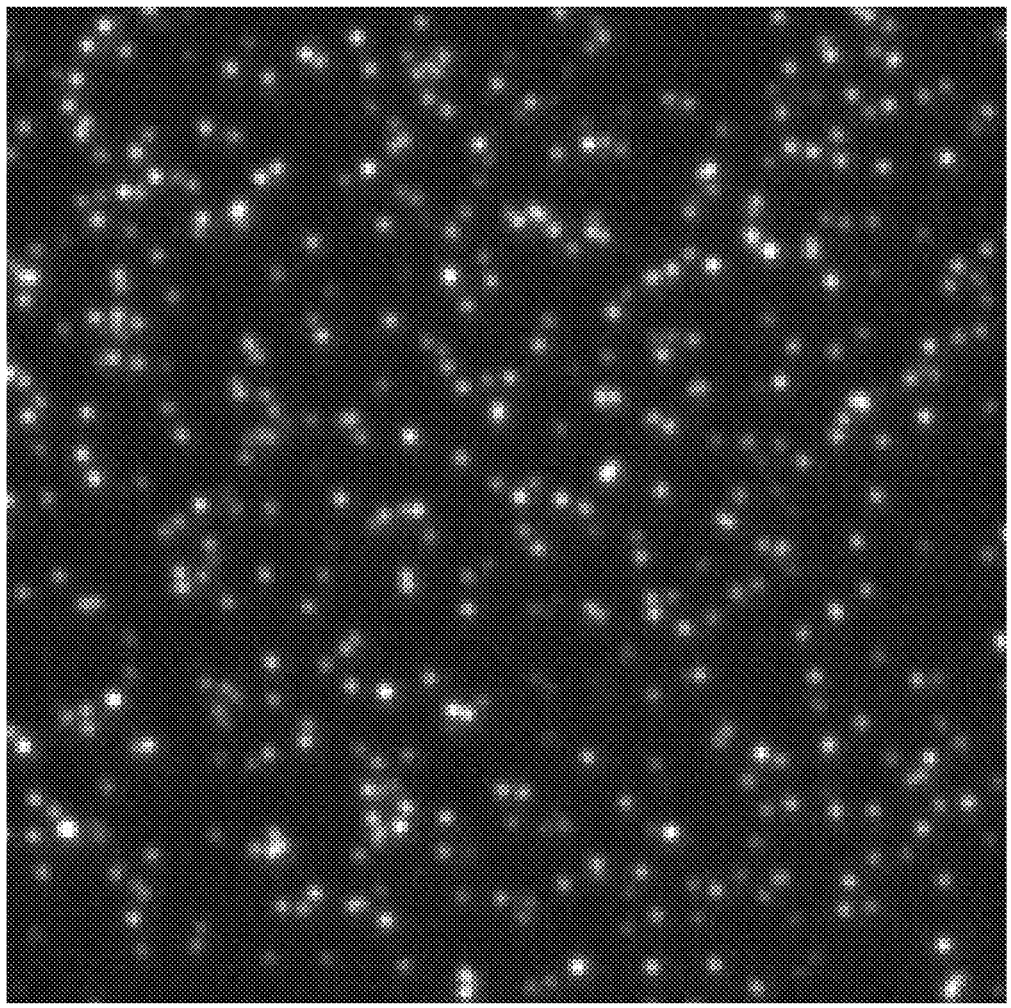
FIG. 16 is an image of single molecules immobilized on a substrate and bound by a probe comprising a fluorophore.

Specifically, cDNA templates corresponding to transcripts generated from the ERCC (External RNA Controls Consortium) control plasmids by T7 transcription were sequenced. The cDNA molecule generated were >350 nucleotides long. The surface was imaged post incorporation of nucleotides by the DNA polymerase and after the cleavage reaction with TCEP. The yellow circle in FIG. 15B indicates the location of the template molecule that was aligned using data from 10 consecutive cycles of dye incorporation. Data indicated ability to manually detect 10 cycles of nucleotide incorporation by manual viewing of images Example 3: Relative Location Determination for Single Molecule Variants FIG. 16 is an image of single molecules immobilized on a substrate and bound by a probe comprising a fluorophore. The molecules are anti-ERK antibodies bound to ERK protein from cell lysate which has been covalently attached to the solid support. The antibodies are labeled with 3-5 fluorophores per molecule. Similar images are attainable with single fluor nucleic acid targets, e.g., during sequencing by synthesis.

Figure 17:
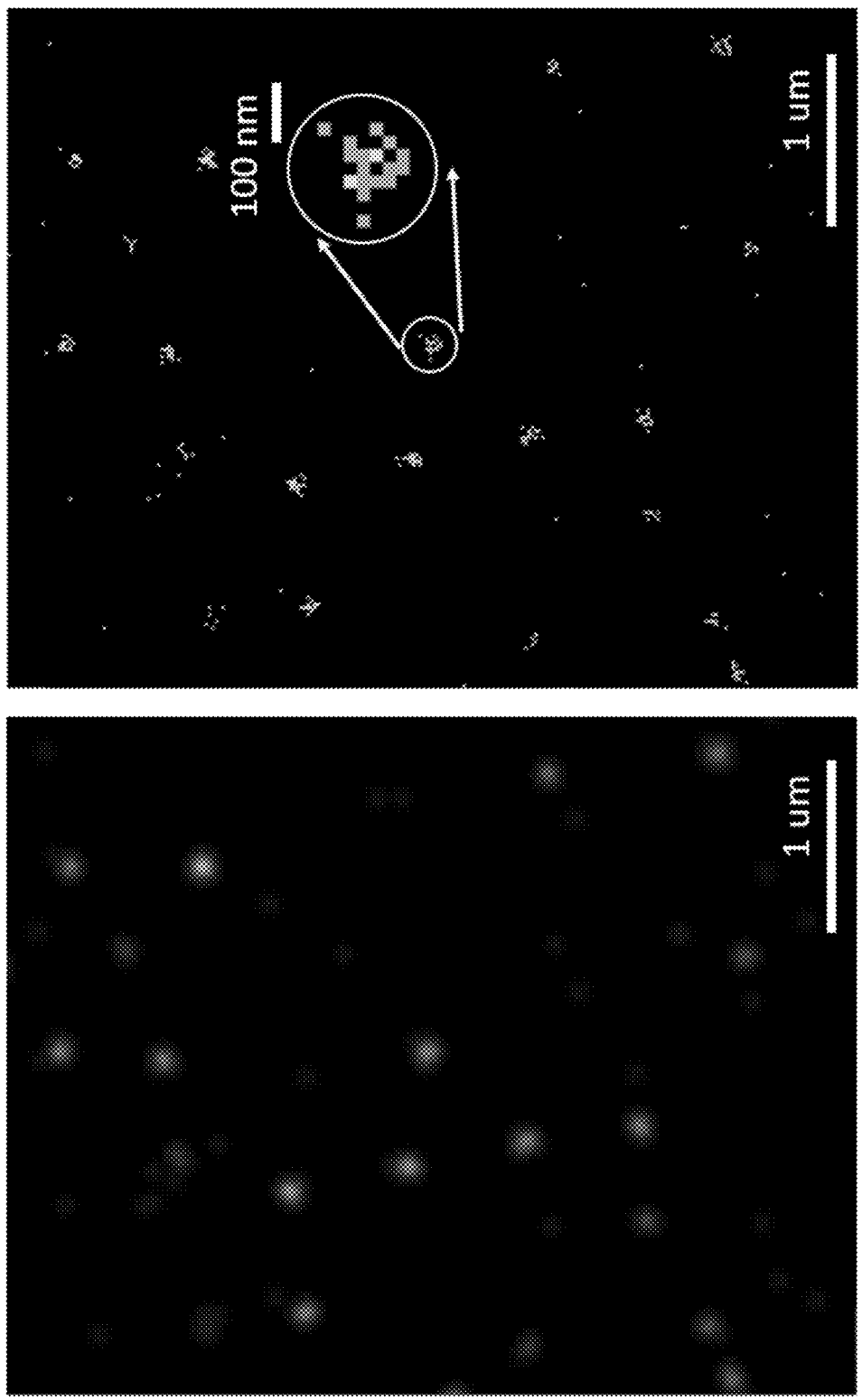
FIG. 17, right panel, shows peaks from oversampled images of a field from each cycle overlaid from several analytes on a substrate (clusters of peaks). The left panel is the smoothed version of the right panel, recapitulating a Gaussian distribution of peaks from an analyte across a plurality of cycles with a highly accurate peak indicating relative positional information.
Figure 18:
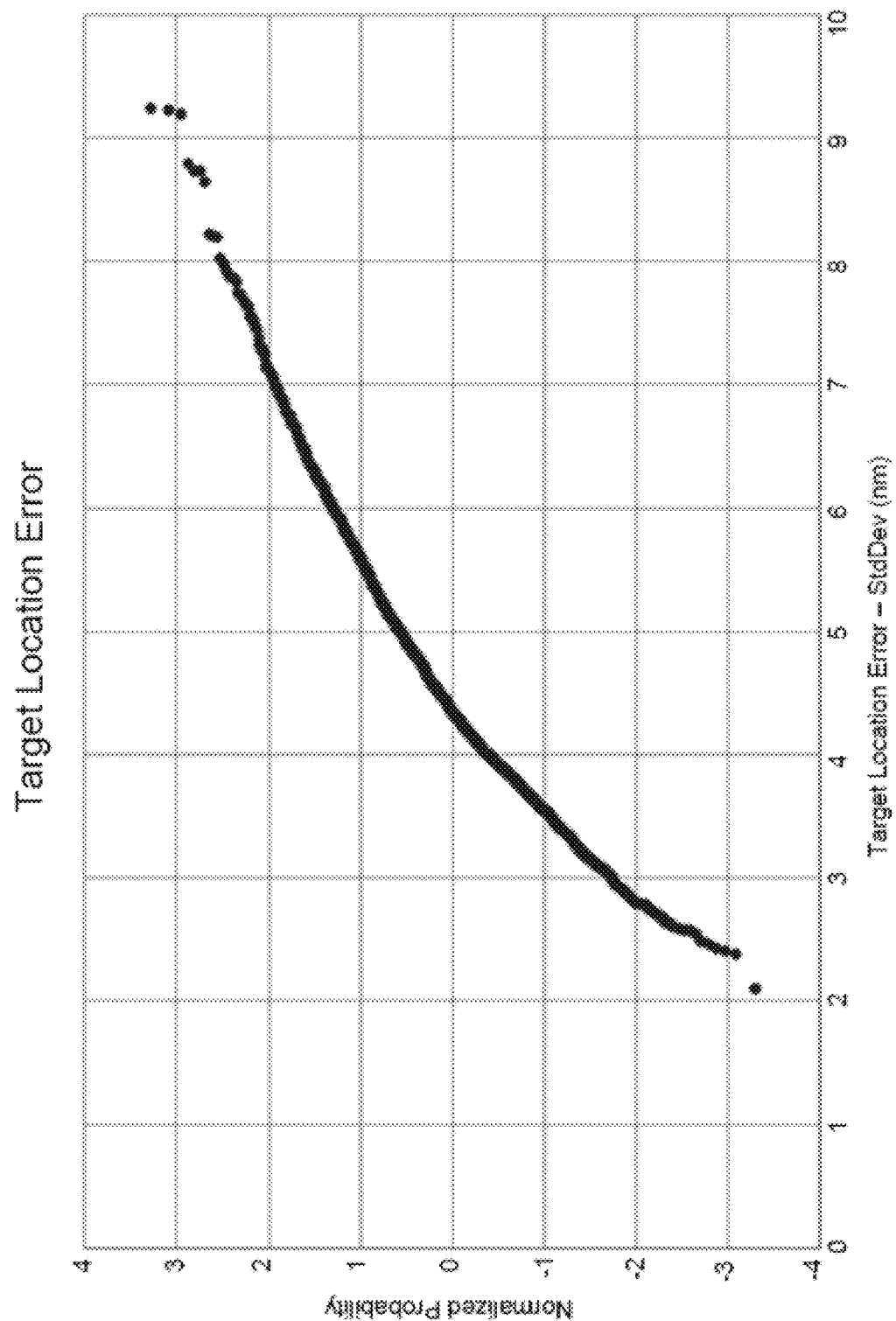
FIG. 18 shows localization variation for each of a plurality of molecules found in a field. The median localization variance is 5 nm and the 3 sigma localization variance is under 10 nm.

To improve accuracy of detection, the molecules undergo successive cycles of probe binding and stripping, in this case 30 cycles. In each round, the image is processed to determine the location of the molecules. The images are background subtracted, oversampled by 2×, after which peaks are identified. Multiple layers of cycles are overlaid on a 20 nm grid. The location variance is the standard deviation or the radius divided by the square root of the number of measurements. FIG. 17, right panel, shows each peak from each cycle overlaid. The left panel is the smoothed version of the right panel. Each bright spot represents a molecule. The molecule locations are resolvable with molecule-to-molecule distances under 200 nm. FIG. 18 shows localization variation for each of a plurality of molecules found in a field. The median localization variance is 5 nm and the 3 sigma localization variance is under 10 nm.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method for processing or analyzing a plurality of analytes, comprising:
   a. providing said plurality of analytes on a substrate, wherein said plurality of analytes is provided on said substrate at a density, wherein a minimum effective pitch between an analyte of said plurality of analytes and an adjacent analyte of said plurality of analytes is less than $\lambda/(2*NA)$, wherein a plurality of optical signals obtained by an optical imaging system have a wavelength $\lambda$, wherein said plurality of optical signals is generated from a plurality of probes over a plurality of cycles of said plurality of probes binding to one or more analytes of said plurality of analytes, and wherein NA comprises a numerical aperture of said optical imaging system;

b. obtaining said plurality of optical signals from said plurality of probes over said plurality of cycles of said plurality of probes binding to said one or more analytes of said plurality of analytes, wherein at least a subset of said plurality of optical signals overlap;

c. processing said plurality of optical signals to identify a position of said one or more analytes of said plurality of analytes; and d. using said position to identify said one or more analytes of said plurality of analytes.

2. The method of claim 1, wherein (b) further comprises overlaying said plurality of optical signals from said plurality of probes over said plurality of cycles of said plurality of probes binding to said one or more analytes of said plurality of analytes to generate an overlay of said plurality of optical signals, and wherein (c) further comprises applying an optical distribution model to said overlay of said plurality of optical signals to determine said position of said one or more analytes of said plurality of analytes.

3. The method of claim 2, wherein said optical distribution model comprises a Gaussian distribution.

4. The method of claim 1, wherein said processing of said plurality of optical signals comprises applying a resolving function to an image of said plurality of optical signals.

5. The method of claim 4, wherein said resolving function comprises nearest neighbor variable regression.

6. The method of claim 4, wherein said resolving function comprises removing interfering optical signals from one or more neighboring analytes using a center-to-center distance between said one or more neighboring analytes.

7. The method of claim 1, wherein said plurality of analytes is provided on said substrate at a density of at least 1 molecule per square micrometer.

8. The method of claim 7, wherein said plurality of analytes is provided on said substrate at a density of at least 4 molecules per square micrometer.

9. The method of claim 7, wherein said plurality of analytes is provided on said substrate at a density of at least 6 molecules per square micrometer.

10. The method of claim 7, wherein said plurality of analytes is provided on said substrate at a density of at least 8 molecules per square micrometer.

11. The method of claim 7, wherein said plurality of analytes is provided on said substrate at a density of at least 12 molecules per square micrometer.

12. The method of claim 1, wherein said optical imaging system comprises a resolution of one pixel per 250 nanometers or lower.

13. The method of claim 1, wherein an oversampled image is generated from said plurality of optical signals with a higher pixel density from a field image for said plurality of cycles of said plurality of probes binding to said one or more analytes of said plurality of analytes provided on said substrate.

14. The method of claim 1, wherein said plurality of probes comprises a labelled nucleotide, an aptamer, an antibody, a polypeptide, an oligonucleotide, or any combination thereof.

15. The method of claim 14, wherein said plurality of probes comprises a labelled nucleotide.

16. The method of claim 1, wherein said plurality of probes comprise a detectable label that is indirectly bound to, hybridized to, conjugated to, or covalently linked to said plurality of probes.

17. The method of claim 16, wherein said detectable label comprises a fluorophore or a chemiluminescent molecule.

18. The method of claim 1, wherein said wavelength of light of said plurality of optical signals is 400 nanometers (nm)-700 nm.

19. The method of claim 1, wherein said N. A. is 0.2-2.0.

20. The method of claim 1, wherein said plurality of optical signals comprises a fluorescent signal.

21. The method of claim 20, wherein said nucleic acid molecule comprises 1 kilo-base (kb) 100 kb.

22. The method of claim 1, wherein at least one analyte of said plurality of analytes comprises a nucleic acid molecule.

23. The method of claim 1, wherein at least one analyte of said plurality of analytes comprises a protein or polypeptide.

24. The method of claim 1, wherein said position is a relative position with respect to another analyte of said one or more analytes of said plurality of analytes.

* * * * *

UNITED STATES PATENT AND TRADEMARK OFFICE
CERTIFICATE OF CORRECTION

PATENT NO. : 11,060,140 B2
APPLICATION NO. : 16/458977
DATED : July 13, 2021
INVENTOR(S) : Staker et al.

Page 1 of 1

It is certified that error appears in the above-identified patent and that said Letters Patent is hereby corrected as shown below:

On the Title Page

Item (74), please correct "Sonso" to "Sonsini"

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*